(12) United States Patent
Doyon et al.

(10) Patent No.: US 9,506,120 B2
(45) Date of Patent: Nov. 29, 2016

(54) RAPID IN VIVO IDENTIFICATION OF BIOLOGICALLY ACTIVE NUCLEASES

(75) Inventors: Yannick Doyon, El Cerrito, CA (US); Fyodor Urnov, Point Richmond, CA (US)

(73) Assignee: Sangamo BioSciences, Inc., Richmond, CA (US)

( * ) Notice: Subject to any disclaimer, the term of this patent is extended or adjusted under 35 U.S.C. 154(b) by 780 days.

(21) Appl. No.: 12/284,887

(22) Filed: Sep. 25, 2008

(65) Prior Publication Data

US 2009/0111119 A1  Apr. 30, 2009

Related U.S. Application Data

(60) Provisional application No. 60/995,566, filed on Sep. 27, 2007.

(51) Int. Cl.
| | | |
|---|---|---|
| C12Q 1/34 | (2006.01) | |
| C12Q 1/68 | (2006.01) | |
| C12N 9/22 | (2006.01) | |
| G01N 33/573 | (2006.01) | |

(52) U.S. Cl.
CPC ............ *C12Q 1/6897* (2013.01); *C12N 9/22* (2013.01); *C12Q 1/34* (2013.01); *G01N 33/573* (2013.01); *G01N 2333/922* (2013.01)

(58) Field of Classification Search
None
See application file for complete search history.

(56) References Cited

U.S. PATENT DOCUMENTS

| | | |
|---|---|---|
| 5,356,802 A | 10/1994 | Chandrasegaran |
| 5,436,150 A | 7/1995 | Chandrasegaran |
| 5,487,994 A | 1/1996 | Chandrasegaran |
| 5,789,538 A | 8/1998 | Rebar et al. |
| 5,925,523 A | 7/1999 | Dove et al. |
| 6,007,988 A | 12/1999 | Choo et al. |
| 6,013,453 A | 1/2000 | Choo et al. |
| 6,140,081 A | 10/2000 | Barbas |
| 6,140,466 A | 10/2000 | Barbas et al. |
| 6,200,759 B1 | 3/2001 | Dove et al. |
| 6,242,568 B1 | 6/2001 | Barbas et al. |
| 6,410,248 B1 | 6/2002 | Greisman et al. |
| 6,453,242 B1 | 9/2002 | Eisenberg et al. |
| 6,479,626 B1 | 11/2002 | Kim et al. |
| 6,534,261 B1 | 3/2003 | Cox et al. |
| 6,599,692 B1 | 7/2003 | Case et al. |
| 6,607,882 B1 | 8/2003 | Cox, III et al. |
| 6,808,710 B1 | 10/2004 | Wood et al. |
| 6,824,978 B1 | 11/2004 | Cox, III et al. |
| 6,903,185 B2 | 6/2005 | Kim et al. |
| 6,933,113 B2 | 8/2005 | Case et al. |
| 6,946,292 B2 | 9/2005 | Kanda et al. |
| 6,979,539 B2 | 12/2005 | Cox, III et al. |
| 7,013,219 B2 | 3/2006 | Case et al. |
| 7,153,949 B2 | 12/2006 | Kim et al. |
| 7,163,824 B2 | 1/2007 | Cox, III et al. |
| 2003/0165997 A1 | 9/2003 | Kim et al. |
| 2003/0232410 A1 | 12/2003 | Liljedahl et al. |
| 2004/0002092 A1 | 1/2004 | Arnould et al. |
| 2005/0026157 A1 | 2/2005 | Baltimore |
| 2005/0064474 A1 | 3/2005 | Urnov et al. |
| 2005/0208489 A1 | 9/2005 | Carroll |
| 2006/0063231 A1 | 3/2006 | Li et al. |
| 2006/0078552 A1 | 4/2006 | Arnould et al. |
| 2006/0153826 A1 | 7/2006 | Arnould et al. |
| 2006/0188987 A1 | 8/2006 | Guschin et al. |
| 2006/0206949 A1 | 9/2006 | Arnould et al. |
| 2007/0117128 A1 | 5/2007 | Smith et al. |
| 2007/0134796 A1 | 6/2007 | Holmes et al. |
| 2008/0131962 A1 | 6/2008 | Miller |
| 2008/0159996 A1 | 7/2008 | Ando et al. |
| 2009/0111119 A1 | 4/2009 | Doyon et al. |

FOREIGN PATENT DOCUMENTS

| | | |
|---|---|---|
| GB | 2338237 A | 12/1999 |
| WO | WO 95/19431 A1 | 7/1995 |
| WO | WO 96/06166 A1 | 2/1996 |
| WO | WO 98/37186 A1 | 8/1998 |
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |
| WO | WO 98/54311 A1 | 12/1998 |
| WO | WO 00/27878 A1 | 5/2000 |
| WO | 0114557 A1 | 3/2001 |
| WO | WO 01/60970 A2 | 8/2001 |
| WO | WO 01/88197 A2 | 11/2001 |
| WO | WO 02/16536 A1 | 2/2002 |
| WO | WO 02/077227 A2 | 10/2002 |
| WO | WO 02/099084 A2 | 12/2002 |
| WO | 03016571 A1 | 2/2003 |
| WO | WO 03/016496 A2 | 2/2003 |
| WO | 03022875 A2 | 3/2003 |

(Continued)

OTHER PUBLICATIONS

Nickoloff et al. Transcription stimulates homologous recombination in mammalian cells. Molecular and Cellular Biology, vol. 10, No. 9, pp. 4837-4845, Sep. 1990.*
Rothstein. One-step gene disruption in yeast. Methods in Enzymology, vol. 101, pp. 202-211, 1983.*
Liang et al. Template topology and transcription: Chromatin templates relaxed by localized linearization are transcriptionally active in yeast. Molecular and Cellular Biology, vol. 17, No. 5, pp. 2825-2834, May 1997.*
Alwin et al. Custom zinc-finger nucleases for use in human cells. Molecular Therapy, vol. 12, pp. 610-617, 2005.*

(Continued)

*Primary Examiner* — Jennifer Dunston

(74) *Attorney, Agent, or Firm* — Pasternak Patent Law; Susan Abrahamson

(57) ABSTRACT

Disclosed herein are methods and compositions for rapidly identifying and ranking nucleases for specific cleavage of a target sequence.

10 Claims, 14 Drawing Sheets

(56) References Cited

FOREIGN PATENT DOCUMENTS

| WO | WO 03/078619 A1 | 9/2003 |
|---|---|---|
| WO | WO 2004/067753 A2 | 8/2004 |
| WO | WO 2005/014791 A2 | 2/2005 |
| WO | WO 2005/084190 A2 | 9/2005 |
| WO | WO 2006/097853 A1 | 9/2006 |
| WO | WO 2007/014275 A2 | 1/2007 |
| WO | WO 2007/014181 A2 | 2/2007 |
| WO | WO 2007/049095 A1 | 5/2007 |
| WO | WO 2007/139898 A2 | 12/2007 |
| WO | WO 2008021207 A2 * | 2/2008 |
| WO | 2009042163 A2 | 4/2009 |
| WO | 2011097036 A1 | 8/2011 |

OTHER PUBLICATIONS

Winzeler et al. Functional characterization of the *S. cerevisiae* genome by gene deletion and parallel analysis. Science, vol. 285, pp. 901-906, Aug. 1999.*
Perez et al. Factors affecting double-strand break-induced homologous recombination in mammalian cells. BioTechniques, vol. 39, pp. 109-115, Jul. 2005.*
HomoloGene Entry 37325, http://www.ncbi.nlm.nih.gov/homologene/37325?report=homologene, downloaded on Dec. 19, 2014, printed as pp. 1/3-3/3.*
UniGene, UGID:3117250, Zm.103089, *Zea mays* (maize) ipp2K, http://www.ncbi.nlm.nih.gov/UniGene/clust.cgi?ORG=Zm&CID=103089, downloaded on Dec. 19, 2014, printed as pp. 1/2-2/2.*
HomoloGene Entry 8422, http://www.ncbi.nlm.nih.gov/homologene/8422, downloaded on Dec. 19, 2014, printed as pp. 1/3-3/3.*
Middelhaufe et al. Domain mapping on the human metastasis regulator protein h-Prune reveals a C-terminal dimerization domain. The Biochemical Journal, vol. 407, No. 2, pp. 199-205, Oct. 2007.*
Prado et al. Role of reciprocal exchange, one-ended invasion crossover and single-strand annealing on inverted and direct repeat recombination in yeast: Different requirements for the RAD1, RAD10, and RAD52 genes. Genetics, vol. 139, pp. 109-123, Jan. 1995.*
Fishman-Lobell, et al., "Removal of Nonhomologous DNA Ends in Double-Strand Break Recombination: The Role of the Yeast Ultraviolet Repair Gene RAD1," *Science* 258:480-484 (1992).
Kandavelou, et al., "Magic Scissors for Genome Surgery," *Nature Biotechnology* 23:686-687 (2005).
Paques, et al., "Two Pathways for Removal of Nonhomologous DNA Ends During Double-Strand Break Repair in *Saccharomyces Cerevisiae,*" *Molecular and Cellular Biology* 17:6765-6771(1997).
Rudin, et al., "Genetic and Physical Analysis of Double-Strand Break Repair and Recombination in *Saccharomyces Cerevisiae,*" *Genetics* 122: 519-534 (1989).
Amould, et al., "Engineering of Large Numbers of Highly Specific Homing Endonucleases That Induce Recombination on Novel DNA Targets," *J. Mol. Biol.* 355:443-458 (2006).
Beerli, et al., "Engineering Polydactyl Zinc-Finger Transcription Factors," *Nature Biotechnology* 20:135-141 (2002).

Chames, et al., "In Vivo Selection of Engineered Homing Endonucleases Using Double-Strand Break Induced Homologous Recombination," *Nucleic Acids Research* 33(20):e178 (2005).
Choo, et al., "Advances in Zinc Finger Engineering," *Curr. Opin. Struct. Biol.* 10:411-416 (2000).
Isalan et al., "A Rapid, Generally Applicable Method to Engineer Zinc Fingers Illustrated by Targeting the HIV-1 Promoter," *Nat Biotechnol* 19:656-660 (2001).
Kim, et al., "Hybrid Restriction Enzymes: Zinc Finger Fusions to FOK I Cleavage Domain," PNAS USA 93:1156-1160 (1996).
Miller, et al., "An Improved Zinc-Finger Nuclease Architecture for Highly Specific Genome Editing," Nat Biotechnology 25:778-785 (2007).
Moehle, et al., "Targeted Gene Addition Into a Specified Location in the Huma•Genome Using Designed Zinc Finger Nucleases," PNAS USA 104:3055-3060 (2007).
Pabo, et al., "Design and Selection of Novel CYS2-HIS2 Zinc Finger Proteins," *Ann. Rev. Biochem.* 70:313-340 (2001).
Segal, et al., "Custom DNA-Binding Proteins Come of Age: Polydactyl Zinc-Finger Proteins," *Curr. Opin. Biotechnol.* 12:632-637 (2001).
Urnov, et al., "Highly Efficient Endogenous Human Gene Correction Using Designed Zinc-Finger Nucleases," *Nature* 435:646-651 (2005).
U.S. Appl. No. 12/284,897, filed Sep. 25, 2008.
Angharad, et al., "Beyond the Antigen Receptor: Editing the Genome of T-Cells for Cancer Adoptive Cellular Therapies," Frontiers in Immunology, 4(1): XPO55110101, doi: 10.3389/fimmu.2013.00221, Aug. 2013.
Dotti, "Blocking PD-1 in Cancer Immunotherapy," Blood 114:1457-1458 (2009).
Durai, et al., Zinc Finger Nucleases: Custom-Designed Molecuar Scissors for Genome Engineering of Plant and Mammalian Cells, Nucleic Acids Research 33(18):5978-5990 (2005).
Genbank Accession No. U64863.1 (Oct. 12, 2005) 3 pages.
Klug, et al., "Towards Therapeutic Applications of Engineered Zinc Finger Proteins," FEBS Letters 892-894 (2005).
Mao and Wu, "Inhibitory RNA Molecules in Immunotherapy for Cancer," Methods Mol. Biol. 623:325-339 (2010).
Okazaki and Honjo, "PD-1 and PD-1 Ligands: From Discovery to Clinical Application," International Immunology 19(7):813-824, 2007.
Edelstein, et al., "Gene Therapy Clinical Trials Worldwide 1984-2004—An Overview," J. Gene Med. 6:597-602 (2004).
Luo, et al., "Synthetic DNA Delivery Systems," Nature Biotechnology 18:33-37 (2000).
Nishimura, et al., "Development of Lupus-Like Autoimmune Diseases by Disruption of the PD-1 Gene Encoding an ITIM Motif-Carrying Immunoreceptor," Immunity 11:141-151 (1999).
Palu, "In Pursuit of New Developments for Gene Therapy for Human Diseases," J. Biotechnol. 68:1-13 (1999).
Verma, et al., "Gene Therapy-Promises, Problems and Prospects," Nature 389:239-242 (1997).
Verma and Weitzman, "Gene Therapy: Twenty-First Century Medicine," Annual Review of Biochemistry 74:711-738 (2005).
Waldman, "Effective Cancer Therapy Through Immunomodulation," Annual Review of Medicine 57:65-81 (2006).
Wong, et al., "Programmed Death-1 Blockade Enhances Expansion and Functional Capacity of Human Melanoma Antigen-Specific CTLS," International Immunity 19(10):1223-1234 (2007).

* cited by examiner

FIG. 3

SEQUENCE LISTING

<160> NUMBER OF SEQ ID NOS: 54

<210> SEQ ID NO 1
<211> LENGTH: 36
<212> TYPE: DNA

```
<213> ORGANISM: Artificial Sequence
<220> FEATURE:
<223> OTHER INFORMATION: Synthetic oligonucleotide

<400> SEQUENCE: 1
aattgtcgac atgtttgctt tctactttct caccgc                              36

<210> SEQ ID NO 2
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 2
aattggatcc ccccattgga gctgcc                                         26

<210> SEQ ID NO 3
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 3
aattgagctc agaccacctg cataataaca gc                                  32

<210> SEQ ID NO 4
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 4
aattgaattc gggcaaaaat tggtaccaat gc                                  32

<210> SEQ ID NO 5
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 5
aattcgtacg tctaactgat ctatccaaaa ctg                                 33

<210> SEQ ID NO 6
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 6
aattgtcgac ttgatctttt ggttttatat ttgttg                              36

<210> SEQ ID NO 7
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 7
tattaggtgt gaaaccacga aaagt                                          25
```

```
<210> SEQ ID NO 8
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 8
actgtcattg ggaatgtctt atgat                                              25

<210> SEQ ID NO 9
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 9
attacgctcg tcatcaaaat ca                                                 22

<210> SEQ ID NO 10
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 10
catgtcttct cgttaagact gcat                                               24

<210> SEQ ID NO 11
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 11
ccatggccaa ctgtgagcgt accttcat                                           28

<210> SEQ ID NO 12
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 12
tctggggata ggcaggtaga ggaatgaa                                           28

<210> SEQ ID NO 13
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 13
tctggggata ggcaggtaga ggaatgaa                                           28

<210> SEQ ID NO 14
<211> LENGTH: 28
<212> TYPE: DNA
<213> ORGANISM: Artificial Sequence
<220> FEATURE:
```

<223> OTHER INFORMATION: Synthetic oligonucleotide

<400> SEQUENCE: 14
tctggggata ggcaggtaga ggaatgaa                                28

<210> SEQ ID NO 15
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 15
tctggggata ggcaggtaga ggaatgaa                                28

<210> SEQ ID NO 16
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 16
gccaactgtg agcgtacctt cattgcga                                28

<210> SEQ ID NO 17
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 17
gccaactgtg agcgtacctt cattgcga                                28

<210> SEQ ID NO 18
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 18
gccaactgtg agcgtacctt cattgcga                                28

<210> SEQ ID NO 19
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 19
gccaactgtg agcgtacctt cattgcga                                28

<210> SEQ ID NO 20
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 20
atggttctgg ggataggcag gtagagga                                28

```
<210> SEQ ID NO 21
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 21
atggttctgg ggataggcag gtagagga                                              28

<210> SEQ ID NO 22
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 22
caaaccagat ggggtccagc ggggtctt                                              28

<210> SEQ ID NO 23
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 23
caaaccagat ggggtccagc ggggtctt                                              28

<210> SEQ ID NO 24
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 24
caaaccagat ggggtccagc ggggtctt                                              28

<210> SEQ ID NO 25
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 25
caaaccagat ggggtccagc ggggtctt                                              28

<210> SEQ ID NO 26
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 26
tcgcaatgaa ggtacgctca cagttggc                                              28

<210> SEQ ID NO 27
<211> LENGTH: 28
<212> TYPE: DNA
<213> ORGANISM: Artificial Sequence
<220> FEATURE:
<223> OTHER INFORMATION: Synthetic oligonucleotide
```

<400> SEQUENCE: 27
tcgcaatgaa ggtacgctca cagttggc                                              28

<210> SEQ ID NO 28
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 28
catgcaagta agtggacttc attgttcc                                              28

<210> SEQ ID NO 29
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 29
catgcaagta agtggacttc attgttcc                                              28

<210> SEQ ID NO 30
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 30
catgcaagta agtggacttc attgttcc                                              28

<210> SEQ ID NO 31
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 31
tttcagacca acaaggcgga atcctttc                                              28

<210> SEQ ID NO 32
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 32
ccatggtgag tgtgcctgtg tgggatac                                              28

<210> SEQ ID NO 33
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 33
ccatggtgag tgtgcctgtg tgggatac                                              28

<210> SEQ ID NO 34
<211> LENGTH: 28

```
<212> TYPE: DNA
<213> ORGANISM: Artificial Sequence
<220> FEATURE:
<223> OTHER INFORMATION: Synthetic oligonucleotide

<400> SEQUENCE: 34
ccatggtgag tgtgcctgtg tgggatac                                              28

<210> SEQ ID NO 35
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 35
aactaccggc cctgagtgca tgtatttc                                              28

<210> SEQ ID NO 36
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 36
aactaccggc cctgagtgca tgtatttc                                              28

<210> SEQ ID NO 37
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 37
aactaccggc cctgagtgca tgtatttc                                              28

<210> SEQ ID NO 38
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 38
cctgggacca tccgtggaga cttctgca                                              28

<210> SEQ ID NO 39
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 39
cctgggacca tccgtggaga cttctgca                                              28

<210> SEQ ID NO 40
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 40
```
ttggagtctg cagggttggt ctccccga                                             28

<210> SEQ ID NO 41
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 41
ttggagtctg cagggttggt ctccccga                                             28

<210> SEQ ID NO 42
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 42
tatacatggc agtgattctg tggagagt                                             28

<210> SEQ ID NO 43
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 43
tatacatggc agtgattctg tggagagt                                             28

<210> SEQ ID NO 44
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 44
tatacatggc agtgattctg tggagagt                                             28

<210> SEQ ID NO 45
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 45
gttcctgggt ggagaaagag atagtcac                                             28

<210> SEQ ID NO 46
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 46
gttcctgggt ggagaaagag atagtcac                                             28

<210> SEQ ID NO 47
<211> LENGTH: 28
<212> TYPE: DNA
<213> ORGANISM: Artificial Sequence

```
<220> FEATURE:
<223> OTHER INFORMATION: Synthetic oligonucleotide

<400> SEQUENCE: 47
gttcctgggt ggagaaagag atagtcac                                       28

<210> SEQ ID NO 48
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 48
gttcctgggt ggagaaagag atagtcac                                       28

<210> SEQ ID NO 49
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 49
acaggagggc agaccacatt gcttttca                                       28

<210> SEQ ID NO 50
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 50
acaggagggc agaccacatt gcttttca                                       28

<210> SEQ ID NO 51
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 51
attcatagat ccagttctga gcacagct                                       28

<210> SEQ ID NO 52
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 52
attcatagat ccagttctga gcacagct                                       28

<210> SEQ ID NO 53
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 53
attcatagat ccagttctga gcacagct                                       28
```

```
<210> SEQ ID NO 54
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 54
attcatagat ccagttctga gcacagct                                              28
```

RAPID IN VIVO IDENTIFICATION OF BIOLOGICALLY ACTIVE NUCLEASES

CROSS-REFERENCE TO RELATED APPLICATIONS

The present application claims the benefit of U.S. Provisional Application No. 60/995,566, filed Sep. 27, 2007, the disclosure of which is hereby incorporated by reference in its entirety.

STATEMENT OF RIGHTS TO INVENTIONS MADE UNDER FEDERALLY SPONSORED RESEARCH

Not applicable.

TECHNICAL FIELD

The present disclosure is in the fields of genome engineering and nuclease identification.

BACKGROUND

Nucleases, including zinc finger nucleases and homing endonucleases such as SceI, that are engineered to specifically bind to target sites have been shown to be useful in genome engineering. For example, zinc finger nucleases (ZFNs) are proteins comprising engineered site-specific zinc fingers fused to a nuclease domain. Such ZFNs have been successfully used for genome modification in a variety of different species. See, for example, United States Patent Publications 20030232410; 20050208489; 20050026157; 20050064474; 20060188987; 20060063231; and International Publication WO 07/014,275, the disclosures of which are incorporated by reference in their entireties for all purposes. These ZFNs can be used to create a double-strand break (DSB) in a target nucleotide sequence, which increases the frequency of homologous recombination at the targeted locus more than 1000-fold. In addition, the inaccurate repair of a site-specific DSB by non-homologous end joining (NHEJ) can also result in gene disruption. Creation of two such DSBs results in deletion of arbitrarily large regions.

Currently, ZFNs specific for particular targets are generally identified using in vitro assays used to identify engineered zinc finger proteins. See, e.g., U.S. Patent Publication No. 20050064474. However, these in vitro assays are time and labor intensive. Furthermore, although in vitro methods accurately identify ZFPs with the desired binding activity, the architecture of ZFNs and the chromatin infrastructure over the target locus in living cells may in some instances hinder the capacity of these in vitro assays to accurately predict in vivo ZFN activity.

In vivo screening assays, particularly in yeast host cells, have been used to select homing endonucleases that bind to target sites other than their cognate binding site. See, e.g., Chames et al. (2005) *Nucleic Acids Res* 33(20):e178; Arnould et al. (2006) *J. Mol. Biol.* 355:443-458; and U.S. Patent Publication Nos. 20070117128; 20060206949; 20060153826; 20060078552; and 20040002092. However, such methods have not been broadly applied to any nuclease, including zinc finger nucleases. Moreover, previously described in vivo methods do not identify biologically active nucleases from a panel of nucleases known to bind to a specific target site, nor from a panel of nucleases known to bind to a set of sites within a particular genomic region. Rather, these previously-described in vivo screening assays utilize a randomly generated library of mutant homing endonucleases to identify proteins which bind to a particular, specific target site. Thus, previously-described assays do not predict in vivo functionality from a collection of nucleases known to bind to a particular target, nor from a collection of nucleases known to bind to a set of distinct targets within a broader genomic region. Nor do these assays accurately determine which nucleases are least toxic to the host cell.

Thus, there remains a need for additional assays to identify specific nucleases, particularly high throughput in vivo assays that identify functional, specifically-targeted nucleases.

SUMMARY

The present disclosure relates to development of nucleases, for example engineered meganucleases and zinc finger nuclease (ZFNs). Specifically, described herein are compositions and methods for the efficient screening, identification, and ranking of biologically active engineered nucleases. In addition, the assay systems described herein also allow for rapid toxicity screening of such nucleases.

The rapid identification of highly active and specific lead nucleases for a particular target gene as described herein significantly alleviates the obstacles associated with repetitive and time-consuming experiments typically performed in diverse cell types and organisms.

In one aspect, described herein is a reporter construct for detecting double-stranded cleavage of a target sequence by one or more nucleases. The reporter construct comprises overlapping and non-functional sequences of a reporter gene separated by a target sequence recognized by the nuclease. The 5' region of the reporter gene may be operably linked to a constitutive or inducible promoter. The reporter gene may encode an enzymatic protein, for example Mel1. Expression of the reporter construct in a host cell results in a signal that is measurable by suitable assays, for example by colorimetric or enzymatic assays performed on intact or lysed cells. In certain embodiments, activity of the reporter gene is determined by assaying levels of a secreted protein (e.g., the product of the reporter gene itself or a product produced directly or indirectly by an active reporter gene product). In certain embodiments, the reporter construct also comprises regions of homology flanking the discontinuous reporter gene sequences and/or a selectable marker. The regions of homology may be to any region of a host cell genome, for example the HO locus in yeast. Optionally, a second reporter gene is also included, for example a reporter that is transcribed only in the presence of double-stranded breaks. In certain embodiments, the reporter construct comprises a construct as shown in FIG. 2 or FIG. 8.

In another aspect, described herein is a host cell (or population of host cells) comprising any of the reporter constructs described herein. The host cell typically includes the cellular machinery (endogenous or exogenous) for processing a double-stranded break to create overlapping single-stranded sequences that are repaired via single-stranded annealing repair. In certain embodiments, the host cell is a yeast cell, for example *S. cerevisiae*. The reporter construct may be transiently expressed in the host cell. Alternatively, the reporter construct is stably integrated into the genome of the host cell.

In yet another aspect, methods of identifying a nuclease that induce(s) cleavage at a specific target site are provided. In certain embodiments, the methods comprise introducing one or more nuclease and/or one or more nuclease-expression constructs encoding a nuclease or a pair of nucleases into a host cell comprising a reporter construct as described herein, the reporter construct comprising a target sequence recognized by the nuclease(s); incubating the cells under conditions such that the nuclease(s) are expressed; and measuring the levels of reporter gene expression in the cells, wherein increased levels of reporter gene expression are correlated with increased nuclease-induced cleavage of the target sequence. The nuclease may comprise, for example, a non-naturally occurring DNA-binding domain (e.g., an engineered zinc finger protein or an engineered DNA-binding domain from a homing endonuclease). In certain embodiments, the nuclease is a zinc finger nuclease (ZFN) or pair of ZFNs.

In yet another aspect, methods of ranking a panel of nucleases for their cleavage-inducing activity at a specific target site are provided. The methods comprise introducing a nuclease of the panel and/or expression constructs encoding nuclease of the panel into separate host cells, the host cells each comprising a reporter construct as described herein, the reporter construct comprising a target sequence recognized by the nuclease(s); incubating the cells under conditions such that the nuclease(s) are expressed; measuring the levels of reporter gene expression in the cells; and ranking the nuclease(s) according to levels of reporter gene activity induced in the host cell. In certain embodiments, the nuclease comprises a ZFN or ZFN pair. In other embodiments, the nuclease comprises a homing endonuclease with an engineered DNA-binding domain and/or a fusion of a DNA-binding domain of a homing nuclease and a cleavage domain of a heterologous nuclease.

In another aspect, methods of predicting the in vivo cleavage activity of a nuclease are provided. The methods comprise introducing the nuclease and/or expression constructs encoding a nuclease into a host cell comprising a reporter construct as described herein, the reporter construct comprising a target sequence recognized by the nuclease; incubating the cells under conditions such that the nuclease is expressed; and measuring the levels of reporter gene expression in the cells; wherein higher levels or reporter gene expression are predictive of a nuclease that will be active in vivo. In certain embodiments, the nuclease comprises a ZFN or ZFN pair. In other embodiments, the nuclease comprises a homing endonuclease with an engineered DNA-binding domain and/or a fusion of a DNA-binding domain of a homing nuclease and a cleavage domain of a heterologous nuclease.

In yet another aspect, methods of determining toxic effects on a host cell caused by a nuclease are provided. The methods comprise introducing a nuclease and/or one or more expression construct(s) encoding one or more nucleases into a host cell; incubating the cells under conditions such that the nuclease(s) are expressed; culturing the cells over a period of time; and measuring the growth of cells in culture at various time intervals. In certain embodiments, the growth of the cells is determined by spectrophotometry, for example by determining the optical density (OD) of the cultured cells at a suitable wavelength (e.g., $OD_{600}$ nm). The time intervals at which cell growth is determined may be, for example, hours or days (e.g., 2 days, 3 days, 4 days, 5 days, 6, days, 7 days, 8 days, 9 days, 10 days, or even longer) after introduction (or induction) of the nuclease expression cassettes. The nuclease may comprises a ZFN, a ZFN pair, a meganuclease with an engineered DNA-binding domain or a fusion of a naturally-occurring or engineered meganuclease DNA-binding domain and a heterologous cleavage domain. Furthermore, the methods can be performed in a host cell comprising the target sequence recognized by the nuclease (e.g., a reporter construct as described herein). Alternatively, the methods may be performed in a host cell that does not contain the target sequence recognized by the nuclease, as a toxic nuclease will delay yeast growth in the presence or absence of its target sequence.

In another aspect, methods of selecting a biologically active nuclease (e.g., ZFN, ZFN pair or homing nuclease) are provided. The methods comprise determining nucleases or that cleaves at a selected target site by any of the methods described herein; and determining the toxicity of the nuclease(s) using any of the methods described herein, wherein biologically active nuclease(s) exhibiting cleavage activity and low toxicity are selected.

In any of the methods described herein, levels of reporter gene activity may be measured directly, for example by directly assaying the levels of the reporter gene product (e.g., GFP fluorescence). Alternatively, levels of the reporter gene can be assayed by measuring the levels of a downstream product (e.g., enzymatic product) of the reaction that requires function of the protein encoded by the reporter gene. In addition, in any of these methods, expression of the nuclease(s) may be driven by a constitutive or inducible promoter. Furthermore, in any of the methods described herein, the nuclease(s) (e.g., ZFN, ZFN pair, engineered homing endonuclease and/or fusion or a naturally occurring or engineered homing endonuclease DNA-binding domain and heterologous cleavage domain) may be known to recognize the target sequence, for example from results obtained from in vitro assay experiments.

BRIEF DESCRIPTION OF THE DRAWINGS

FIG. 3 shows in vitro binding data obtained for various ZFNs targeted to the NME1 locus. The sequences shown correspond to SEQ ID NOS: 11 through 54, respectively.

FIG. 4, panels A and B, are graphs showing results from SSA annealing assays and toxicity studies for NME-ZFNs.

FIG. 7A shows MEL1 activity of the ZFN pairs shown on the x-axis in yeast cells containing the MEL1 reporter construct with inserted PD1 target sequence. The left bar shows MEL1 activity in the yeast cells prior to induction of expression of the indicated ZFN pairs and the right bar shows MEL1 activity in the yeast cells 6 hours after induction of expression of the indicated ZFN pairs.

FIG. 7B depicts growth, as measured by spectrophotometry at OD$_{600}$, of yeast host cells containing the MEL1 reporter constructs containing the PD1 target sequence at various times after introduction of the NME1-targeted ZFN pairs indicated on the x-axis. The left bar shows OD$_{600}$ of the yeast cells prior to transfection with the indicated ZFN pairs and the right bar shows OD$_{600}$ of the yeast cells 30 hours after introduction of the indicated ZFN pairs.

FIG. 9A shows MEL1 activity of the ZFN pairs shown on the x-axis in yeast cells containing the MEL1 reporter construct with inserted golden target sequence. The left-most bar shows MEL1 activity in the yeast cells prior to induction of the ZFN expression with galactose with the indicated ZFN pairs; the bar 2$^{nd}$ from the left shows MEL1 activity in the yeast cells 2 hours after induction of expression of the indicated ZFN pairs; the bar 2$^{nd}$ from the right shows MEL1 activity in the yeast cells 4 hours after induction of expression of the indicated ZFN pairs; and the right-most bar shows MEL1 activity in the yeast cells 6 hours after induction of expression of the indicated ZFN pairs.

FIG. 9B depicts growth, as measured by spectrophotometry at OD$_{600}$, of yeast host cells containing the MEL1 reporter constructs containing the zebrafish golden target sequence at various times after introduction of the golden-targeted ZFN pairs indicated on the x-axis. The left-most bar shows OD$_{600}$ of the yeast cells prior to transfection with the indicated ZFN pairs; the bar 2$^{nd}$ from the left shows OD$_{600}$ of the yeast cells 23 hours after introduction of the indicated ZFN pairs; the bar 2$^{nd}$ from the right shows OD$_{600}$ of the yeast cells 27 hours after introduction of the indicated ZFN pairs; and the right-most bar shows OD$_{600}$ of the yeast cells 30 hours after introduction of the indicated ZFN pairs.

FIG. 10A shows MEL1 activity of the ZFN pairs shown on the x-axis in yeast cells containing the MEL1 reporter construct with inserted notail target sequence. The left-most bar shows MEL1 activity in the yeast cells prior to induction of the ZFN expression with galactose with the indicated ZFN pairs; the bar 2$^{nd}$ from the left shows MEL1 activity in the yeast cells 2 hours after induction of expression of the indicated ZFN pairs; the bar 2$^{nd}$ from the right shows MEL1 activity in the yeast cells 4 hours after induction of expression of the indicated ZFN pairs; and the right-most bar shows MEL1 activity in the yeast cells 6 hours after induction of expression of the indicated ZFN pairs.

FIG. 10B depicts growth, as measured by spectrophotometry at OD$_{600}$, of yeast host cells containing the MEL1 reporter constructs containing the zebrafish notail target sequence at various times after introduction of the notail-targeted ZFN pairs indicated on the x-axis. The left-most bar shows OD$_{600}$ of the yeast cells prior to transfection with the indicated ZFN pairs; the bar 2$^{nd}$ from the left shows OD$_{600}$ of the yeast cells 23 hours after introduction of the indicated ZFN pairs; the bar 2$^{nd}$ from the right shows OD$_{600}$ of the yeast cells 27 hours after introduction of the indicated ZFN pairs; and the right-most bar shows OD$_{600}$ of the yeast cells 30 hours after introduction of the indicated ZFN pairs.

FIG. 12A shows a wild-type zebrafish embryo. FIG. 12B shows a zebrafish embryo when the notail gene was mutated as described in Amacher et al. (2002) Development 129(14): 3311-23. FIG. 12C shows a zebrafish embryo with ntl$^{+/-}$ genotype and FIG. 12D shows a zebrafish embryo with a ntl$^{+/-}$ genotype injected with 5 ng of ZFN mRNA directed against notail gene.

DETAILED DESCRIPTION

Figure 1:
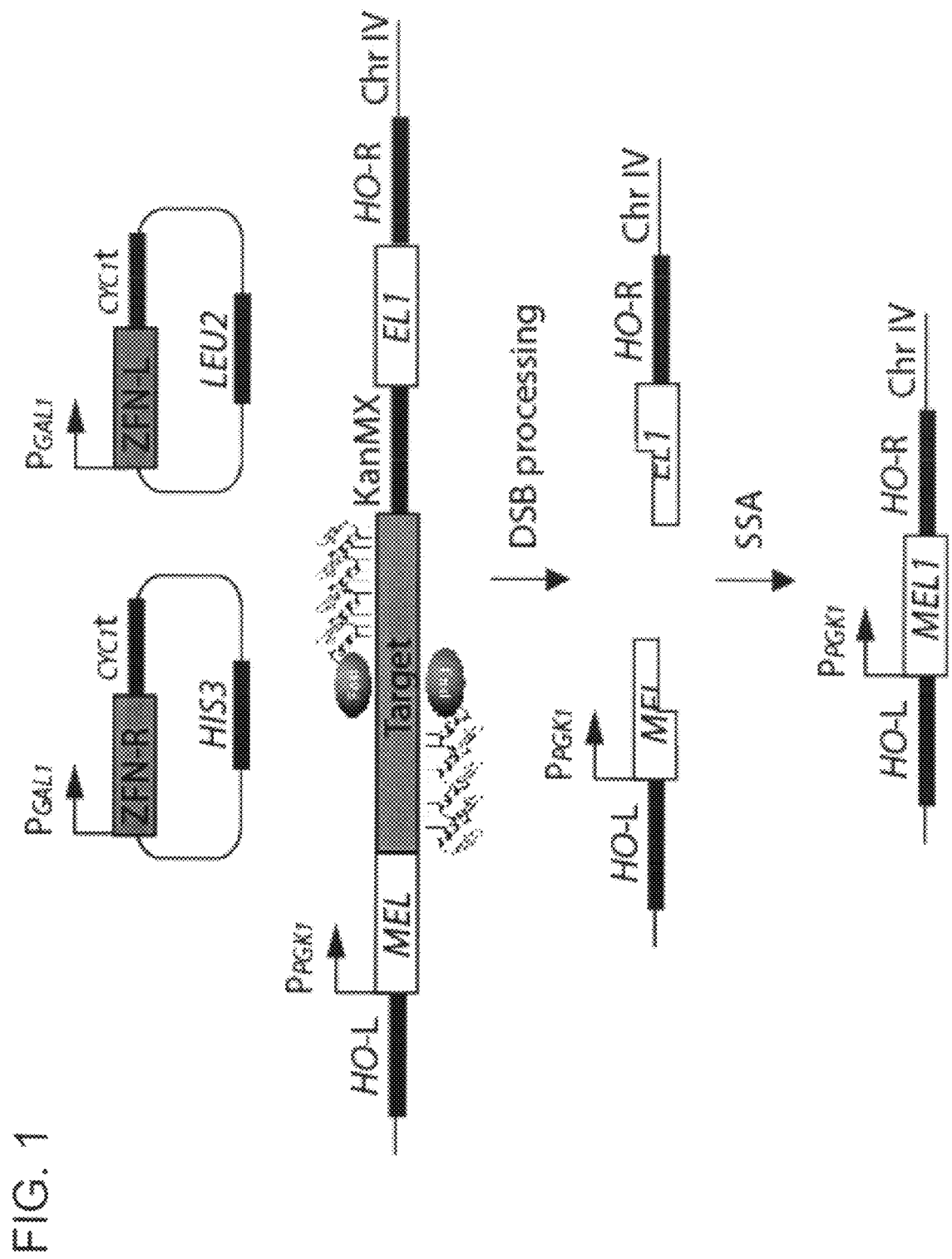
FIG. 1 is a schematic depicting detection of ZFN activity using a single stranded annealing (SSA)-based reporter system. "$P_{GAL1}$" refers to a GAL1 promoter driving expression of a zinc finger nuclease (ZFN1 or ZFN2); "$_{CYC1}t$" refers to a CYC1 transcription terminator; "HIS3" refers to a wild-type yeast gene HIS3 which complements specific auxotrophic mutations in yeast (His- phenotype); "LEU2" refers to a wild-type yeast gene LEU2 which complements specific auxotrophic mutations in yeast (Leu- phenotype); "HO-L" refers to the left homology arm of the reporter construct which targets the reporter to the HO locus; "HO-R" refers to the right homology arm of the reporter construct which targets the reporter to the HO locus; "$P_{PGK1}$" refers to a portion of a PGK1 promoter; "MEL" and "EL1" refer to a sequence, which when operably linked, encodes a functional Mel1 enzyme; "target" refers to a sequence containing target site(s) for the ZFNs; "KanMX" refers to a sequence encoding kanamycin resistance; "ChrIV" refers to chromosome IV; "DSB" refers to double stranded break processing; "SSA" refers to single strand annealing.

Described herein are compositions and methods for high throughput in vivo screening systems for identifying functional nucleases. In particular, the assays use a reporter system to monitor the ability of a nuclease to induce a double-stranded break at their target site. In addition, the assays can be used to determine the effect of the nuclease on cell growth (toxicity).

Engineered nuclease technology is based on the engineering of naturally occurring DNA-binding proteins. For example, engineering of homing endonucleases with tailored DNA-binding specificities has been described. Chames et al. (2005) *Nucleic Acids Res* 33(20):e178; Arnould et al. (2006) *J. Mol. Biol.* 355:443-458. In addition, engineering of ZFPs has also been described. See, e.g., U.S. Pat. Nos. 6,534,261; 6,607,882; 6,824,978; 6,979,539; 6,933,113; 7,163,824; and 7,013,219.

In addition, ZFPs have been attached to nuclease domains to create ZFNs—a functional entity that is able to recognize its intended gene target through its engineered (ZFP) DNA binding domain and the nuclease causes the gene to be cut near the ZFP binding site. See, e.g., Kim et al. (1996) *Proc Natl Acad Sci USA* 93(3):1156-1160. More recently, ZFNs have been used for genome modification in a variety of organisms. See, for example, United States Patent Publications 20030232410; 20050208489; 20050026157; 20050064474; 20060188987; 20060063231; and International Publication WO 07/014,275.

Although the rules that allow engineering of ZFPs to bind to specific DNA sequences are well characterized and accurately identify specific ZFPs, these same ZFPs may not bind with equal affinity and/or specificity when incorporated into a ZFN. For example, it is likely that the chromosomal substrate can affect the precise dimerization of nuclease domains in living cells, consequently diminishing the cleavage potential, and that the precise chromatin architecture over a given genomic locus will differentially affect the ability of ZFNs to bind and cleave their intended target sequence. In addition, it is difficult if not impossible for in vitro assays to mimic the search parameters that a designed DNA binding domain is subjected to when presented with a cellular genome in chromatinized form. As a result, it is essential to test numerous variants in the relevant organism, or cell lineage, to identify a ZFN displaying the optimal characteristics for gene modification.

Furthermore, since every in vivo system has its own peculiarities, it is necessary to develop specific detection assays to determine ZFN action. Thus, unlike previously described in vivo screening methods which screen for homing endonucleases with binding specificity different from the naturally occurring homing endonuclease, the methods described herein provide a rapid and efficient way of ranking nucleases already known to bind to a particular target site by predicting their in vivo functionality as well as the toxicity of a nuclease to the host cell.

Thus, the methods and compositions described herein provide highly efficient and rapid methods for identifying nucleases that are biologically active in vivo. In addition to accurately predicting in vivo nucleases functionality, the assays described herein also can be used to determine nuclease toxicity, thereby allowing identification of the safest and most functionally active proteins.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

Zinc finger binding domains can be "engineered" to bind to a predetermined nucleotide sequence. Non-limiting examples of methods for engineering zinc finger proteins are design and selection. A designed zinc finger protein is a protein not occurring in nature whose design/composition results principally from rational criteria. Rational criteria for design include application of substitution rules and computerized algorithms for processing information in a database storing information of existing ZFP designs and binding data. See, for example, U.S. Pat. Nos. 6,140,081; 6,453,242; and 6,534,261; see also WO 98/53058; WO 98/53059; WO 98/53060; WO 02/016536 and WO 03/016496.

A "selected" zinc finger protein is a protein not found in nature whose production results primarily from an empirical process such as phage display, interaction trap or hybrid selection. See e.g., U.S. Pat. No. 5,789,538; U.S. Pat. No. 5,925,523; U.S. Pat. No. 6,007,988; U.S. Pat. No. 6,013,453; U.S. Pat. No. 6,200,759; WO 95/19431; WO 96/06166; WO 98/53057; WO 98/54311; WO 00/27878; WO 01/60970 WO 01/88197 and WO 02/099084.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

An "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and – cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. patent application Ser. Nos. 10/912,932 and 11/304,981 and U.S. Provisional Application No. 60/808,486 (filed May 25, 2006), incorporated herein by reference in their entireties.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

A "target site" or "target sequence" is a nucleic acid sequence that defines a portion of a nucleic acid to which a binding molecule will bind, provided sufficient conditions for binding exist. For example, the sequence 5'-GAATTC-3' is a target site for the Eco RI restriction endonuclease.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP DNA-binding domain and a cleavage domain) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

"Eukaryotic" cells include, but are not limited to, fungal cells (such as yeast), plant cells, animal cells, mammalian cells and human cells (e.g., T-cells).

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP DNA-binding domain is fused to a cleavage domain, the ZFP DNA-binding domain and the cleavage domain are in operative linkage if, in the fusion polypeptide, the ZFP DNA-binding domain portion is able to bind its target site and/or its binding site, while the cleavage domain is able to cleave DNA in the vicinity of the target site.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

A "reporter gene" or "reporter sequence" refers to any sequence that produces a protein product that is easily measured, preferably in a routine assay. Suitable reporter genes include, but are not limited to, Mel1, chloramphenicol acetyl transferase (CAT), light generating proteins, and β-galactosidase.

Overview

Described herein are compositions and methods for the identification of nucleases that cleave their target sites with the highest frequency and are not toxic to the host cell. Reporter constructs comprising a target site for the nucleases to be tested are described as are host cells comprising these reporter constructs. In the methods described herein, the reporter construct comprising the target site for the nuclease(s) is introduced into a host cell (e.g., yeast cell) to create a reporter strain. When the nuclease(s) are expressed in the cell and induce a double stranded break (DSB) at their target site (e.g., induce a double-stranded break), the reporter gene is reconstituted by the host cell's single-stranded annealing (SSA) machinery. Expression of the reporter gene is readily determined by standard techniques and the levels of reporter gene expression reflect the ability of the nuclease to cleave at the target site. In addition, the host cells can be readily assayed to determine the effect of nuclease expression on cell growth.

Thus, described herein are rapid and efficient high throughput screening methods for determining the most active and least toxic nucleases from a panel of nucleases known to bind to a particular target site. In addition to allowing ranking of nucleases according to their activity at the target locus, the present disclosure also allows for a determination as to which nucleases display non-specific cutting of the genome.

The reagents and methods described herein that allow for in vivo characterization of nuclease action can be conducted in budding yeast. The rapid and versatile genetics of yeast allows testing of a large panel of nucleases in a simple assay in high throughput fashion. The reagents and systems can be used to screen nucleases designed against any gene from any organism and the disclosure has been validated as correctly identifying the optimally active nuclease pairs using lower vertebrate, plant, and human cell cultures.

Reporter Constructs

The methods and systems described herein make use of a reporter constructs comprising a sequence containing a target sequence for the nucleases to be tested. The reporter construct is designed so that the reporter gene is functional only when the target sequence is cleaved and the reporter reconstituted by single-strand annealing (SSA) of the reporter gene sequences. Typically, a reporter construct is generated such that any nuclease target sequence(s) can be readily inserted into the middle of the reporter gene sequence, for example via a polylinker (see, FIGS. 1 and 2).

One or more target sites for the nuclease(s) to be screened can be inserted into the reporter constructs by any suitable methodology, including PCR or commercially available cloning systems such as TOPO® and/or Gateway® cloning systems. In certain embodiments, the target site comprises a concatamer of target sites. See, also, Example 1. Target sites can be from prokaryotic or eukaryotic genes, for example, mammalian (e.g., human), yeast or plant cells.

Any reporter gene that provides a detectable signal can be used, including but not limited, enzymes that catalyze the production of a detectable product (e.g. proteases, nucleases, lipases, phosphatases, sugar hydrolases and esterases). Non-limiting examples of suitable reporter genes that encode enzymes include, for example, MEL1, CAT (chloramphenicol acetyl transferase; Alton and Vapnek (1979) Nature 282:864 869), luciferase, β-galactosidase, β-glucuronidase, β-lactamase, horseradish peroxidase and alkaline phosphatase (e.g., Toh, et al. (1980) Eur. J. Biochem. 182:231 238; and Hall et al. (1983) J. Mol. Appl. Gen. 2:101). Reporter genes that provide a detectable signal directly may also be employed, for example, fluorescent proteins such as, for example, GFP (green fluorescent protein). Fluorescence is detected using a variety of commercially available fluorescent detection systems, including a fluorescence-activated cell sorter (FACS) system for example.

In certain embodiments, the reporter gene encodes an enzyme, for example MEL1. The use of the secreted MEL1 reporter gene allows for convenient detection of recombination events directly from the growth media without requirement for cell lysis, as compared to the classic β-galactosidase yeast reporter gene (Aho et al. (1997) *Anal Biochem* 253:270-272).

Figure 2:
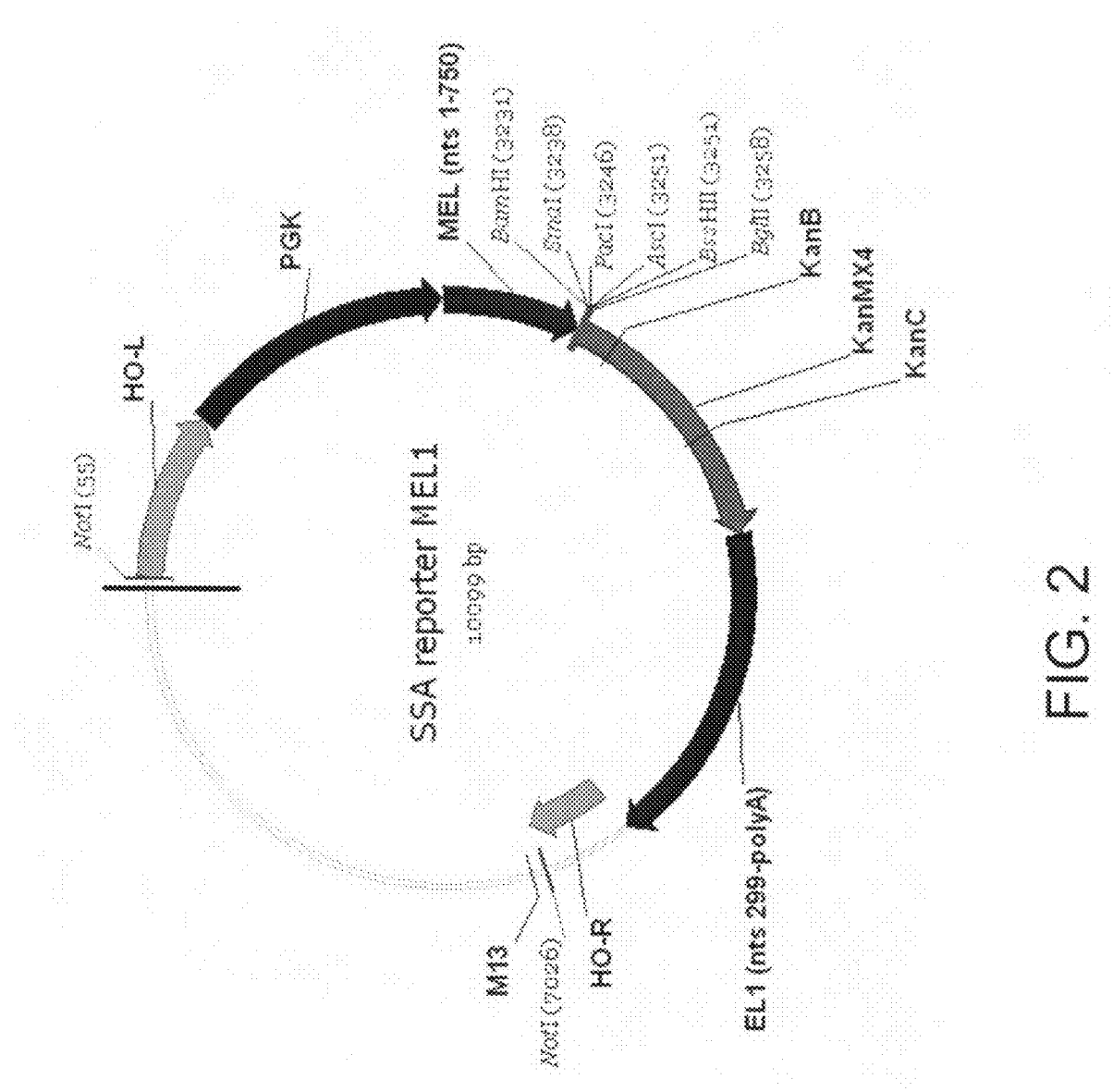
FIG. 2 is a schematic depicting an exemplary SSA MEL1 reporter construct.

As shown in FIGS. 1 and 2, the reporter construct also typically comprises sequences flanking the reporter-target-reporter sequences that are homologous to regions of the host cell genomic DNA. These "homology arms" allow for targeted integration of the reporter construct into the host cell to generate a stable reporter host cell line. The homology arms can be to any genomic sequence of the host cell. Preferably, the homology arms direct insertion of the reporter construct to a non-essential site in the host cell genome, for example the HO locus in yeast. Other non-limiting examples of suitable insertion sites include auxotrophy markers such as URA3, LYS2, and TRP1. Preferably, the reporter construct is inserted into a locus whose mutation (or knockout) does not quantitatively affect host cell growth. The reporter constructs may be integrated into the host cell genome using standard techniques. See, e.g., Chames et al., supra and Arnould et al., supra. Alternatively, the reporter constructs can be maintained episomally.

The reporter constructs may also comprise one or more selectable markers. Positive selection markers are those polynucleotides that encode a product that enables only cells that carry and express the gene to survive and/or grow under certain conditions. For example, cells that express antibiotic resistance genes (e.g. Kan$^r$ or Neo$^r$) gene are resistant to the antibiotics or their analogs (e.g. G418), while cells that do not express these resistance genes are killed in the presence of antibiotics. Other examples of positive selection markers including hygromycin resistance, Zeocin™ resistance and the like will be known to those of skill in the art (see, Golstein and McCusker (1999) *Yeast* 15:1541-1553). Negative selection markers are those polynucleotides that encode a produce that enables only-cells that carry and express the gene to be killed under certain conditions. For example, cells that express thymidine kinase (e.g., herpes simplex virus thymidine kinase, HSV-TK) are killed when gancyclovir is added. Other negative selection markers are known to those skilled in the art. The selectable marker need not be a transgene and, additionally, reporters and selectable markers can be used in various combinations.

The reporter construct may also include additional reporter genes, for example genes that reflect off-target nuclease activity by indicating that the cell is undergoing a DNA damage response (DDR). Non-limiting examples of such suitable additional off-target reporters include genes known to be upregulated by induction of even a single DSB, for example RNR2, RNR4, DIN7, PCL5, DUN1. See, also, Lee et al. (2000) *Cold Spring Harb Symp Quant Biol.* 65:303:314. Additional reporters can be independently introduced and may be transiently expressed or stably integrated into the host cell.

Host Cells

Any host cell that reconstitutes a functional reporter upon cleavage of the target sequence by the nuclease(s) can be used in the practice of the present disclosure. The cell types can be cell lines or natural (e.g., isolated) cells such as, for example, primary cells. Cell lines are available, for example from the AMERICAN TYPE CULTURE COLLECTION™ (ATCC™), or can be generated by methods known in the art, as described for example in Freshney et al., Culture of Animal Cells, A Manual of Basic Technique, 3rd ed., 1994, and references cited therein. Similarly, cells can be isolated by methods known in the art. Other non-limiting examples of cell types include cells that have or are subject to pathologies, such as cancerous cells and transformed cells, pathogenically infected cells, stem cells, fully differentiated cells, partially differentiated cells, immortalized cells and the like. Prokaryotic (e.g., bacterial) or eukaryotic (e.g., yeast, plant, fungal, piscine and mammalian cells such as feline, canine, murine, bovine, porcine and human) cells can be used, with eukaryotic cells being preferred. Suitable mammalian cell lines include CHO (Chinese hamster ovary) cells, HEP-G2 cells, BaF-3 cells, Schneider cells, COS cells (monkey kidney cells expressing SV40 T-antigen), CV-1 cells, HuTu80 cells, NTERA2 cells, NB4 cells, HL-60 cells and HeLa cells, 293 cells (see, e.g., Graham et al. (1977) J. Gen. Virol. 36:59), and myeloma cells like SP2 or NS0 (see, e.g., Galfre and Milstein (1981) Meth. Enzymol. 73(B):3 46. Other eukaryotic cells include, for example, insect (e.g., sp. *frugiperda*), fungal cells, including yeast (e.g., *S. cerevisiae, S. pombe, P. pastoris, K. lactis, H. polymorpha*), and plant cells (Fleer, R. (1992) Current Opinion in Biotechnology 3:486 496).

In a preferred embodiment, the host cell is a yeast cell. Yeast cells are advantageously employed because the deletion of the intervening sequences required for the reconstitution of the reporter is an efficient process in these cells and permits the scanning of large genomic targets. Yeast cells survive the introduction of a DSB even if the target is up to 25 kb (Vaze et al. (2002) *Mol Cell* 10:373-385). In addition, as long as 400 base pairs of homologous regions within the reporter construct are provided, 100% of yeast cells survive to the break using the SSA repair pathway (Sugawara et al. (2000) *Mol Cell Biol* 20:5300-5309). Any strain of yeast cell can be used, including, by way of example, 69-1B or BY4741.

Nucleases

The methods and compositions described herein are broadly applicable and may involve any nuclease of interest. Non-limiting examples of nucleases include meganucleases and zinc finger nucleases. The nuclease may comprise heterologous DNA-binding and cleavage domains (e.g., zinc finger nucleases; meganuclease DNA-binding domains with heterologous cleavage domains) or, alternatively, the DNA-binding domain of a naturally-occurring nuclease may be altered to bind to a selected target site (e.g., a meganuclease that has been engineered to bind to site different than the cognate binding site).

In certain embodiment, the nuclease is a meganuclease (homing endonuclease). Naturally-occurring meganucleases recognize 15-40 base-pair cleavage sites and are commonly grouped into four families: the LAGLIDADG family, the GIY-YIG family, the His-Cyst box family and the HNH family. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. No. 5,420,032; U.S. Pat. No. 6,833,252; Belfort et al. (1997) *Nucleic Acids Res.* 25:3379-3388; Dujon et al. (1989) *Gene* 82:115-118; Perler et al. (1994) *Nucleic Acids Res.* 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue.

DNA-binding domains from naturally-occurring meganucleases, primarily from the LAGLIDADG family, have been used to promote site-specific genome modification in plants, yeast, *Drosophila*, mammalian cells and mice, but this approach has been limited to the modification of either homologous genes that conserve the meganuclease recognition sequence (Monet et al. (1999), Biochem. Biophysics. Res. Common. 255: 88-93) or to pre-engineered genomes into which a recognition sequence has been introduced (Route et al. (1994), Mol. Cell. Biol. 14: 8096-106; Chilton et al. (2003), Plant Physiology. 133: 956-65; Puchta et al. (1996), Proc. Natl. Acad. Sci. USA 93: 5055-60; Rong et al. (2002), Genes Dev. 16: 1568-81; Gouble et al. (2006), J. Gene Med. 8(5):616-622). Accordingly, attempts have been made to engineer meganucleases to exhibit novel binding specificity at medically or biotechnologically relevant sites (Porteus et al. (2005), Nat. Biotechnol. 23: 967-73; Sussman et al. (2004), J. Mol. Biol. 342: 31-41; Epinat et al. (2003), Nucleic Acids Res. 31: 2952-62; Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66; U.S. Patent Publication Nos. 20070117128; 20060206949; 20060153826; 20060078552; and 20040002092). In addition, naturally-occurring or engineered DNA-binding domains from meganucleases have also been operably linked with a cleavage domain from a heterologous nuclease (e.g., FokI).

In other embodiments, the nuclease is a zinc finger nuclease (ZFN). ZFNs comprise a zinc finger protein that has been engineered to bind to a target site in a gene of choice and cleavage domain or a cleavage half-domain.

Zinc finger binding domains can be engineered to bind to a sequence of choice. See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416. An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

Selection of target sites; ZFNs and methods for design and construction of fusion proteins (and polynucleotides encoding same) are known to those of skill in the art and described in detail in U.S. Patent Application Publication Nos. 20050064474 and 20060188987, incorporated by reference in their entireties herein.

In addition, as disclosed in these and other references, zinc finger domains and/or multi-fingered zinc finger proteins may be linked together using any suitable linker sequences, including for example, linkers of 5 or more amino acids in length. See, e.g., U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

Nucleases such as ZFNs and/or meganucleases also comprise a nuclease (cleavage domain, cleavage half-domain). As noted above, the cleavage domain may be heterologous to the DNA-binding domain, for example a zinc finger DNA-binding domain and a cleavage domain from a nuclease or a meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., SI Nuclease; mung bean nuclease; pancreatic DNase I; micrococcal nuclease; yeast HO endonuclease; see also Linn et al. (eds.) Nucleases, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a zinc finger binding domain and two Fok I cleavage half-domains can also be used. Parameters for targeted cleavage and targeted sequence alteration using zinc finger-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Publication WO 07/014,275, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Patent Publication Nos. 20050064474 and 20060188987 and in U.S. application Ser. No. 11/805,850 (filed May 23, 2007), the disclosures of all of which are incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains.

Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E: I499L". The engineered cleavage half-domains described herein are obligate heterodimer mutants in which aberrant cleavage is minimized or abolished. See, e.g., Example 1 of U.S. Provisional Application No. 60/808,486 (filed May 25, 2006), the disclosure of which is incorporated by reference in its entirety for all purposes.

Engineered cleavage half-domains described herein can be prepared using any suitable method, for example, by site-directed mutagenesis of wild-type cleavage half-domains (Fok I) as described in Example 5 of U.S. Patent Publication No. 20050064474 and Example 38 of U.S. Patent Provisional Application Ser. No. 60/721,054.

Nuclease expression constructs can be readily designed using methods known in the art. See, e.g., United States Patent Publications 20030232410; 20050208489; 20050026157; 20050064474; 20060188987; 20060063231; and International Publication WO 07/014,275. In certain embodiments, expression of the nuclease is under the control of an inducible promoter, for example the galactokinase promoter which is activated (de-repressed) in the presence of raffinose and/or galactose and repressed in presence of glucose. In particular, the galactokinase promoter is induced and the nuclease(s) expressed upon successive changes in the carbon source (e.g., from glucose to raffinose to galactose). Other non-limiting examples of inducible promoters include CUP1, MET15, PHO5, and tet-responsive promoters.

Identification of Biologically Active Nucleases

The host cell containing SSA reporter constructs as described herein can be used to identify the most active and the least toxic nucleases from a panel of nucleases engineered to bind to a particular target site. The systems of the present disclosure take advantage of a particular pathway of homology-directed repair (HDR) called single-strand annealing (SSA). If a double-strand break (DSB) occurs between two flanking homologous regions, repair of the broken chromosome results in a deletion containing a single copy of the repeated sequence (Paques and Haber (1999) *Microbiol Mol Biol Rev* 63:349-404). The engineering of a reporter construct containing two overlapping and non-functional parts of a reporter gene separated by a target sequence permits the easy detection of a nuclease-induced DSB.

As outlined in FIG. 1, identification of nucleases with the highest in vivo cleavage activity begins with introduction of a reporter construct. The reporter construct can be episomal, for example, using an episome, for example using a yeast centromeric plasmid (YCp). Preferably, the reporter construct is integrated into the genome of the host cell (e.g., yeast), for example by homologous recombination.

After genotyping the strain for the correct integration of the reporter, the host strain is transformed with nuclease expression vectors. Preferably, nuclease expression is inducible (e.g. galactose-inducible) so that nuclease expression can be induced for a selected amount of time by changing the carbon source in the culture media. After a recovery period required for the cell machinery to repair the induced DSBs, the activity of the reconstituted reporter gene (e.g. Mel1 enzyme) is determined from an aliquot of the media using a suitable (e.g. a colorimetric) assay.

The activity obtained for each nuclease reflects quantitatively its capacity to induce a DSB within the chromosomal target sequence. The activity is typically normalized to the density of the cells in the culture.

The in vivo screening systems described herein have the added benefit of concomitantly interrogating the entire yeast genome for off-target cleavage by the nuclease(s). The host cells also contain the machinery for a second pathway of DSB repair, namely non-homologous end joining (NHEJ). In the haploid state, yeast cells respond inefficiently to a persistent DSB induced by the continued presence of an endonuclease. Only 0.1% of the cells can survive this type of DSB resulting in a strong delay in growth of the population (Moore and Haber, 1996). Such off-target activity will kill most of the cells and, as cell growth can be easily monitored by spectrophotometric determination of cell density within the culture, nucleases that are least toxic to cells (presumably by virtue of their specificity and lack of off-target cleavage) can be readily identified.

Furthermore, off-target effects can also be monitored by utilizing a "gain of signal" assay that exploits the DNA damage response (DDR) pathway. Several genes are known to be upregulated by the induction of even a single DSB (Lee et al. (2000) *Cold Spring Harb Symp Quant Biol* 65:303-

314). Accordingly, any of the compositions or methods described herein may further include a second reporter gene under the control of a promoter that is transcribed only in the presence of DSB. Activity of this second reporter gene can be used to detect broadly non-specific nuclease(s).

Figure 8:
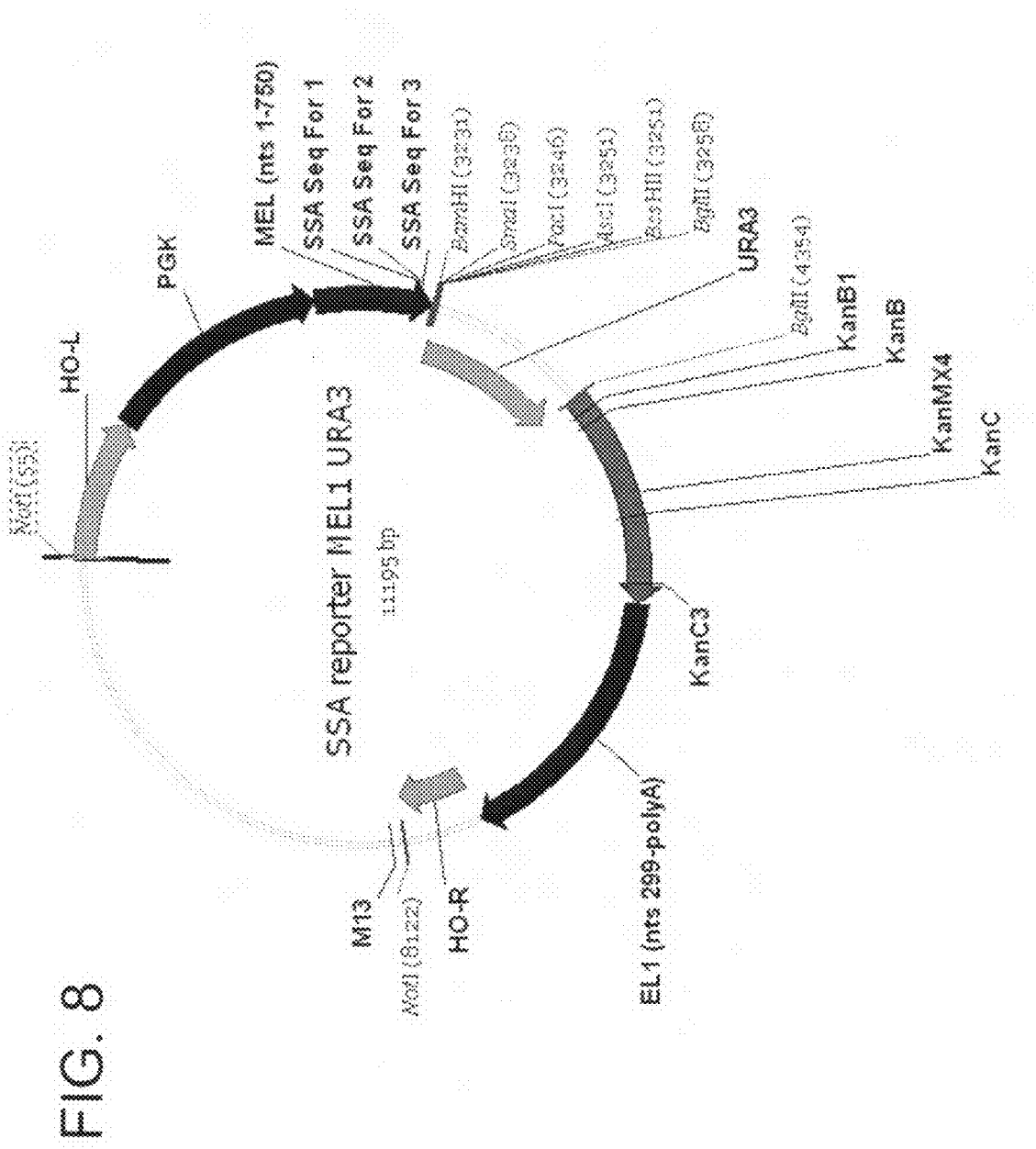
FIG. 8 is a schematic depicting an exemplary SSA MEL1 counter-selectable SSA reporter construct.

A counterselectable gene can also be inserted, for example, in between the interrupted MEL1 gene. This would allow for the selection of active variants from a population of mutated ZFN. Any counterselectable gene can be used, including but not limited to URA3 (FIG. 8). A negative selection can be performed with this gene based on the specific inhibitor, 5-fluoro-orotic acid (FOA) that prevents growth of the prototrophic strains but allows growth of the ura3 mutants. Ura3-cells (arising from SSA) can be selected on media containing FOA. The URA3+ cells, which contain non active ZFN, are killed because FOA is converted to the toxic compound 5-fluorouracil by the action of decarboxylase, whereas ura3-cells are resistant. The negative selection on FOA media is highly discriminating, and usually less than 10-2 FOA-resistant colonies are Ura+.

Thus, reporter strains containing this type of counterselectable marker gene are used to eliminate inactive variants, which typically constitute the vast majority of mutants generated in such genetic screens. Cells containing active variants would be resistant to FOA because the URA3 gene will be deleted during the repair of the DSB by SSA. This kind of selection diminishes significantly the work load since most non-functional colonies/variants are eliminated from the screen.

The following Examples relate to exemplary embodiments of the present disclosure in which the nuclease comprises a ZFN. It will be appreciated that this is for purposes of exemplification only and that other nucleases can be used, for instance homing endonucleases (meganuclases) with engineered DNA-binding domains and/or fusions of naturally occurring of engineered homing endonucleases (meganuclases) DNA-binding domains and heterologous cleavage domains.

EXAMPLES

Example 1

Engineering of a Yeast Reporter Construct

A SSA reporter construct (see, FIG. 2) targeted to the HO locus was generated using the yeast integrating plasmid (Yip) HO-poly-KanMX-HO (Voth et al. (2001) *Nucleic Acids Res* 29:E59-59) as follows. A fragment corresponding to nucleotides 1 to 750 of the MEL1 gene (Liljestrom (1985) *Nucleic Acids Res* 13:7257-7268) (relative to the ATG) was cloned into the SalI and BamHI sites of HO-poly-KanMX-HO using the following primers: 5'-aattgtcgacatgtttgctttc-tactttctcaccgc-3' (SEQ ID NO:1) and 5'-aattggatcccccattg-gagctgcc-3' (SEQ ID NO:2). Subsequently, a fragment from nucleotides 299 to 2100 were cloned into the SacI and EcoRI sites using the following oligos: 5'-aattgagctcagaccacctg-cataataacagc-3' (SEQ ID NO:3) and 5'-aattgaattcgggcaaaaat-tggtaccaatgc-3' (SEQ ID NO:4). Finally, a 1489 base pair fragment of the PGK1 promoter was cloned into the BsiWI and SalI sites using the following oligos: 5'-Aattcg-tacgtctaactgatctatccaaaactg-3' (SEQ ID NO:5) and 5'-Aatt-gtcgacttgatcttttggttttatatttgttg-3' (SEQ ID NO:6).

MEL1 reporter constructs as described above were further modified to include a Gateway® cassette (Invitrogen), following the manufacturer's instructions. In addition, reporter constructs were generated that included shortened versions of the PGK1 promoter. Constructs lacking the ampicillin resistance gene were also generated.

Reporter constructs including various ZFN target sites for were also generated. Briefly, one or more copies of the target sites were generated by PCR or by concatamerization and inserted into the Gateway® MEL1 reporter construct using standard molecular biology techniques. Concatamers were constructed electronically using DNAworks (available on the internet) which designed overlapping oligos that tiled across the target site concatamer. The oligos were used to synthesize the synthetic target site concatamer and a two-step cloning process used to introduce the concatamer into the reporter construct. First, the concatamer was cloned into an entry vector (TOPO®, Invitrogen, CA). In the second step, the concatamer was transferred from the entry vector to the MEL1 reporter using the Gateway® LR Clonase™ system (Invitrogen), essentially as described by the manufacturer. Reporter constructs containing target sites for CCR5-, IPP2K-, and POU5F1/Oct3/4-targeted ZFNs were generated and used for normalization.

Example 2

Integration of the Reporter Construct into Yeast

The integration of the reporter construct into the 69-1B strain (S288C background; MaTα his3Δ200 lys2-128δleu2Δ1) was performed as described (Voth et al. (2001) *Nucleic Acids Res* 29:E59-59). The correct integration was confirmed by Colony PCR using the following oligos: HO-L: 5'-TATTAGGTGTGAAACCACGAAAAGT-3' (SEQ ID NO:7); 5'-ACTGTCATTGGGAATGTCTTAT-GAT-3' (SEQ ID NO:8); HO-R: 5'-attacgctcgtcatcaaaatca-3' (SEQ ID NO:9); and 5'-CATGTCTTCTCGTTAAGACTG-CAT-3' (SEQ ID NO:10).

Example 3

ZFN Activity Assay

To demonstrate that cleavage at the target site of the reporter construct restores MEL1 activity, the following experiments were performed. A SSA reporter construct was engineered as described above to include a recognition site of the HO endonuclease and integrated into host cells as described above. The cells were then transfected with expression vectors encoding the HO endonuclease and the cells cultured in the presence or absence of galactose.

Results are summarized in Table 1.

TABLE 1

Cleavage at target site of the reporter construct restores MEL1 activity

| Host Cell | Expression construct | Galactose | MEL1 Activity |
|---|---|---|---|
| Reporter - no HO target site | empty vector | − | − |
| Reporter - no HO target site | empty vector | + | − |
| Reporter - no HO target site | pGAL HO | − | − |
| Reporter - no HO target site | pGAL HO | + | − |
| Reporter with HO target site | empty vector | − | − |
| Reporter with HO target site | empty vector | + | − |
| Reporter with HO target site | pGAL HO | − | −/+ |
| Reporter with HO target site | pGAL HO | + | +++ |

As shown in Table 1, MEL1 activity was only observed in the presence of the HO endonuclease, and of its target in the reporter locus. Furthermore, essentially no MEL1 gene activity was observed when HO expression was not induced, with the exception of very low-frequency spontaneous MEL1 restoration events. Induction of HO endonuclease expression converted essentially 100% of the cells in the sample to a MEL1 state.

Example 4

Identification of Persistently Biologically Active NME-specific ZFNs

Figure 3:
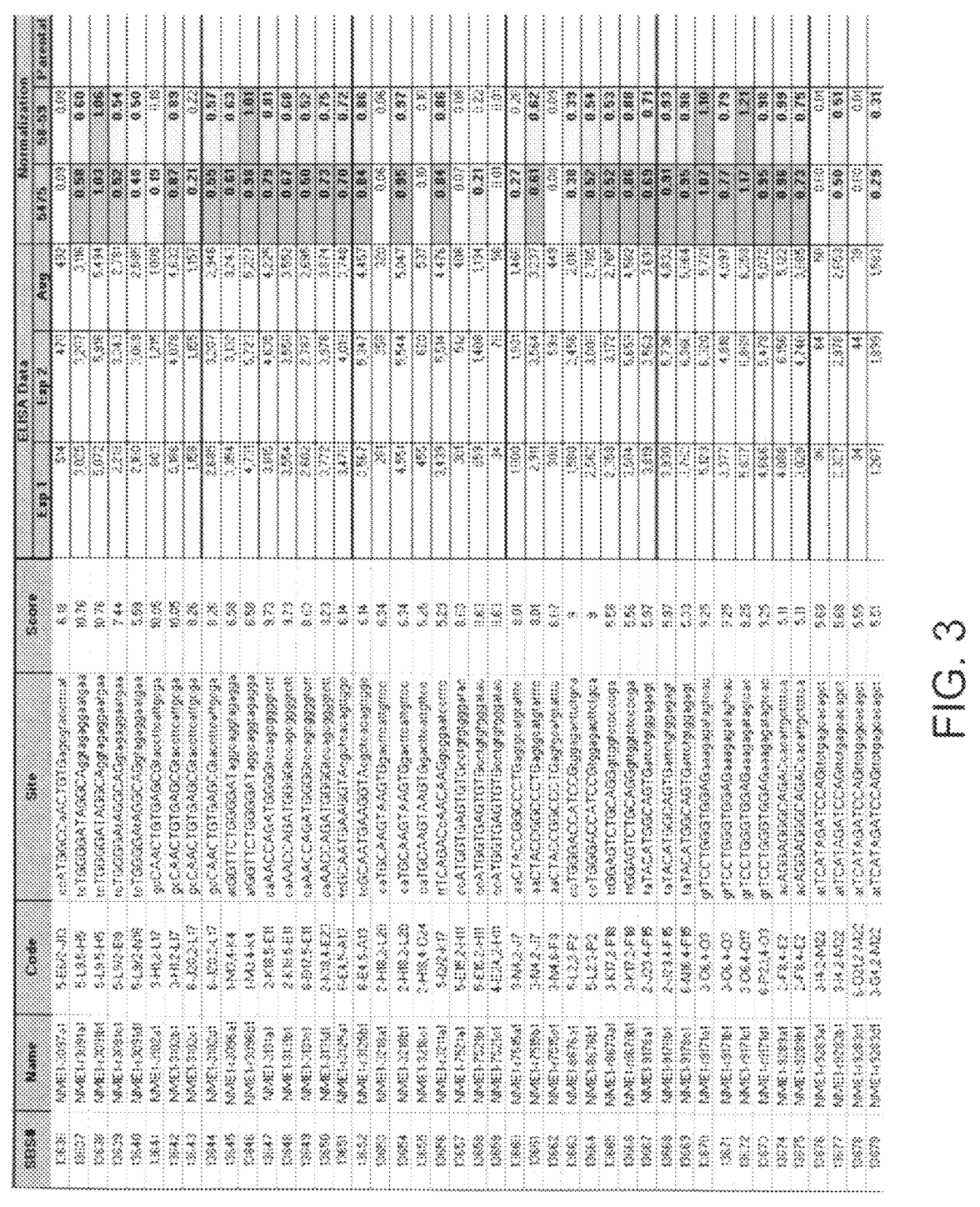

ZFNs were designed to recognize sequences within NME and plasmids comprising sequences encoding these designed NME ZFNs were constructed essentially as described in Urnov et al. (2005) Nature 435(7042):646-651. The ZFNs were tested in in vitro assays (ELISA). FIG. 3 shows the information about the NME-binding ZFNs and their DNA binding characteristics in vitro.

For in vivo screening, the coding sequences of the ZFNs were transferred to galactose inducible expression vectors using standard cloning procedures (Moehle et al. (2007) *Proc Natl Acad Sci USA* 104:3055-3060; Mumberg et al. (1994) *Nucleic Acids Res* 22:5767-5768; Urnov et al. (2005) *Nature* 435:646-651).

The NME1 cDNA (RZPD IRAUp969A091D6) target site was subcloned into the reporter construct and the resulting reporter construct was integrated into the genome of the yeast strain as described in Example 2.

A. Reporter Activity

Expression constructs encoding NME1-targeted ZFN pairs were transformed into the reporter strain in deep well blocks as described in Gietz and Woods, (2006) *Methods Mol Biol* 313:107-120. In order to eliminate the cumbersome manipulation of Petri dishes, pools of transformants were selected in liquid media. Briefly, the cells were resuspended in 1 ml of SC His-Leu-media and incubated for 48 hours at 30° C. To further enrich for transformants, a 1:10 dilution of the pool was incubated in fresh media for another 24 hours.

To de-repress the GAL1 promoter, the pools of transformants were diluted 1:10 into 1 mL of SC His-Leu- media containing 2% raffinose as a source of carbon and incubated O/N at 30° C. ZFN expression was induced by diluting the raffinose cultures 1:10 into 1 ml of SC His-Leu- media containing 2% galactose. Cells were then incubated for various amount of time, typically from 2 to 6 hours, before addition of 2% glucose to stop expression. Cells were then incubated overnight to allow for DSB repair and reporter gene expression.

In order to normalize the reporter signal to the amount of cells in the culture, spectrophotometric readings of the well blocks were taken at 600 nm. The deep well block was then centrifuged at 3000 g for 5 minutes to pellet yeast cells and 10 µl of the media is assayed for Mel1 activity as described in Chen et al. (2004) *Anal Biochem* 335:253-259 and Ryan et al. (1998) *Mol Cell Biol* 18:1774-1782.

Figure 4A:
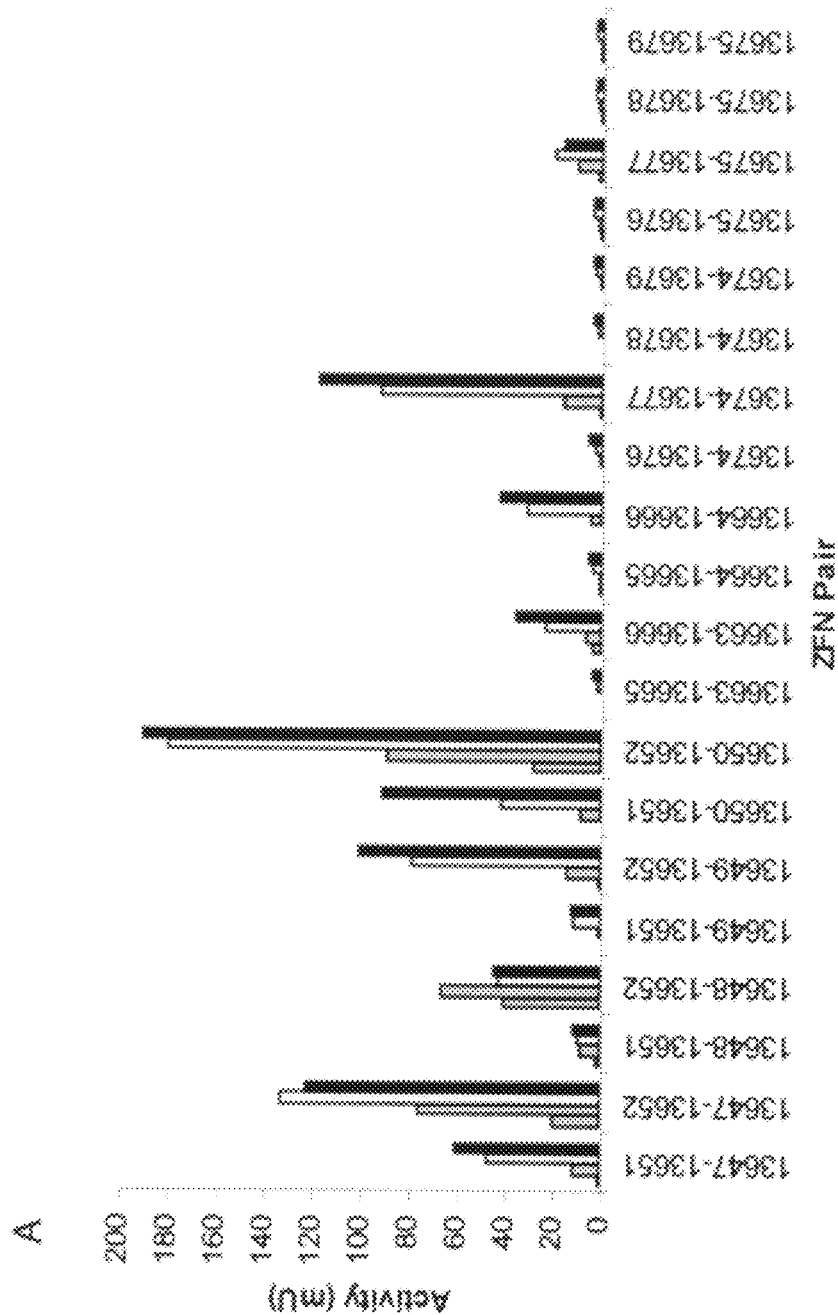
FIG. 4A shows MEL1 activity of the ZFN pairs shown on the x-axis in yeast cells containing the MEL1 reporter construct with inserted NME1 target sequence. The leftmost bar shows MEL1 activity in the yeast cells prior to induction of the ZFN expression with galactose with the indicated ZFN pairs; the bar $2^{nd}$ from the left shows MEL1 activity in the yeast cells 2 hours after induction of expression of the indicated ZFN pairs; the bar 2$^{nd}$ from the right shows MEL1 activity in the yeast cells 4 hours after induction of expression of the indicated ZFN pairs; and the right-most bar shows MEL1 activity in the yeast cells 6 hours after induction of expression of the indicated ZFN pairs.

Results of reporter gene expression are shown in FIG. 4A. The ZFN pairs are indicated below the bars. For each pair, the left-most bar shows Mel1 activity prior to introduction of the indicated ZFN pairs, the second bar from the left shows Mel1 activity 2 hours after the indicated ZFN pairs are introduced into the cells; the third bar from the left shows Mel1 activity 4 hours after the indicated ZFN pairs are introduced into the cells; and the right-most bar shows Mel1 activity 6 hours after the indicated ZFN pairs are introduced into the cells. As shown, there is no Mel1 activity in the absence of an active ZFN pair. Furthermore, although all ZFN pairs were active to some degree, the assay provided a ranking of the most active pairs.

B. Toxicity

To evaluate toxicity of the various ZFNs, ZFN expression was induced by diluting the raffinose cultures 1:100 into 1 ml of SC His-Leu-media containing 2% galactose. Cells were then incubated for various amount of time, typically from 24 to 30 hours. Growth of the populations were then determined by spectrophotometry reading at 600 nm.

Figure 4B:
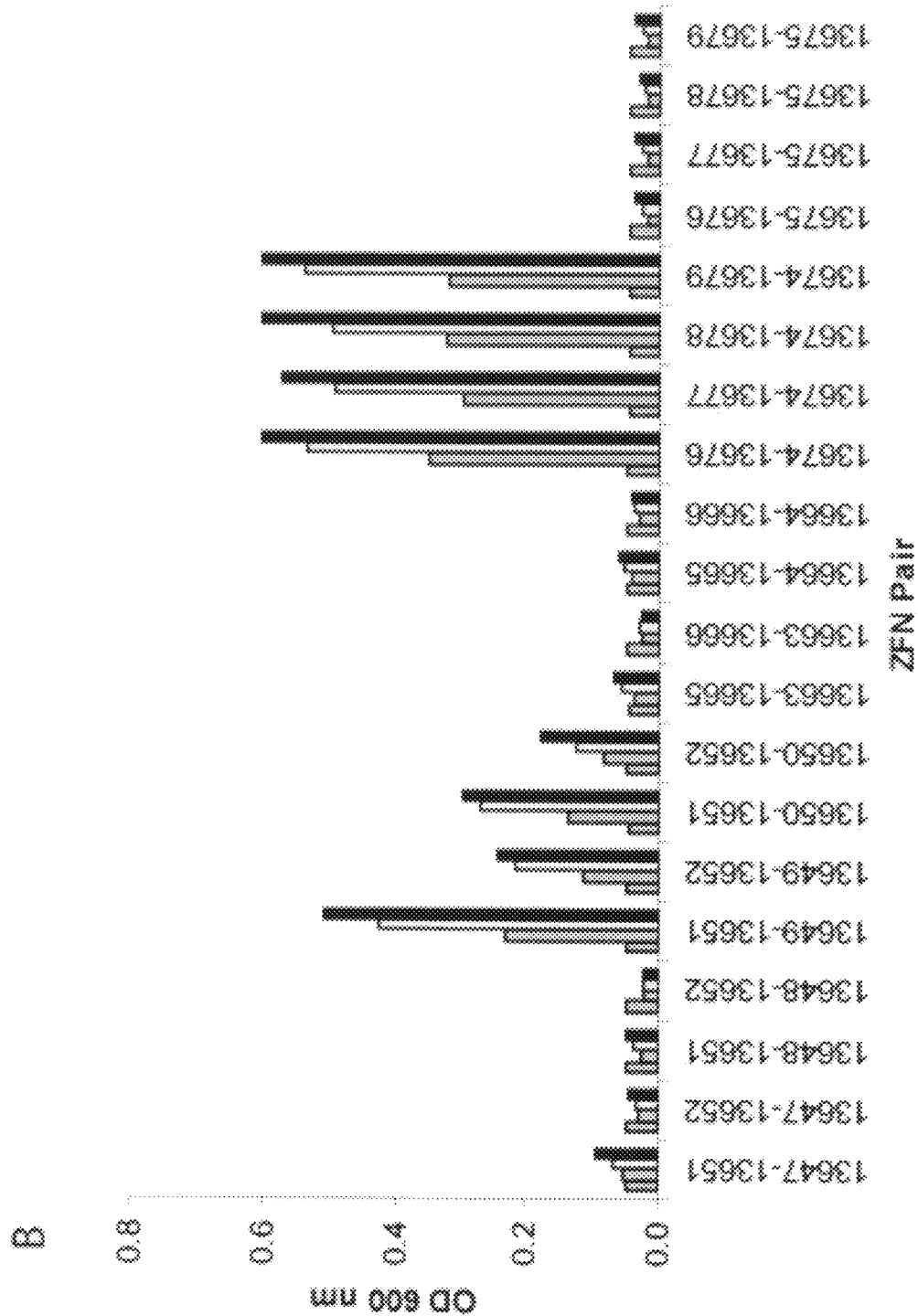
FIG. 4B depicts growth, as measured by spectrophotometry at OD$_{600}$, of yeast host cells containing the MEL1 reporter constructs containing the NME1 target sequence at various times after introduction of the NME1-targeted ZFN pairs indicated on the x-axis. The left-most bar shows OD$_{600}$ of the yeast cells prior to transfection with the indicated ZFN pairs; the bar 2$^{nd}$ from the left shows OD$_{600}$ of the yeast cells 23 hours after introduction of the indicated ZFN pairs; the bar 2$^{nd}$ from the right shows OD$_{600}$ of the yeast cells 27 hours after introduction of the indicated ZFN pairs; and the right-most bar shows OD$_{600}$ of the yeast cells 30 hours after introduction of the indicated ZFN pairs.

Yeast cell growth in the presence of ZFNs is shown in FIG. 4B. The ZFN pairs are indicated below the bars. For each pair, the left-most bar shows OD600 prior to introduction of the indicated ZFN pairs, the second bar from the left shows OD600 readings 23 hours after the indicated ZFN pairs are introduced into the cells; the third bar from the left shows $OD_{600}$ 27 hours after the indicated ZFN pairs are introduced into the cells; and the right-most bar shows OD600 30 hours after the indicated ZFN pairs are introduced into the cells. As shown, yeast cells grow normally in the presence of certain ZFN pairs.

C. Yeast Screen Predicts in vivo Activity

Various active ZFN pairs identified in the reporter activity assay (FIG. 4A) were then transformed into human K562 and tested for their ability to induce mutations in the NME 1 locus, as described in Miller et al. (2007) *Nat. Biotechnol.* 25(7):778-85.

Figure 5:
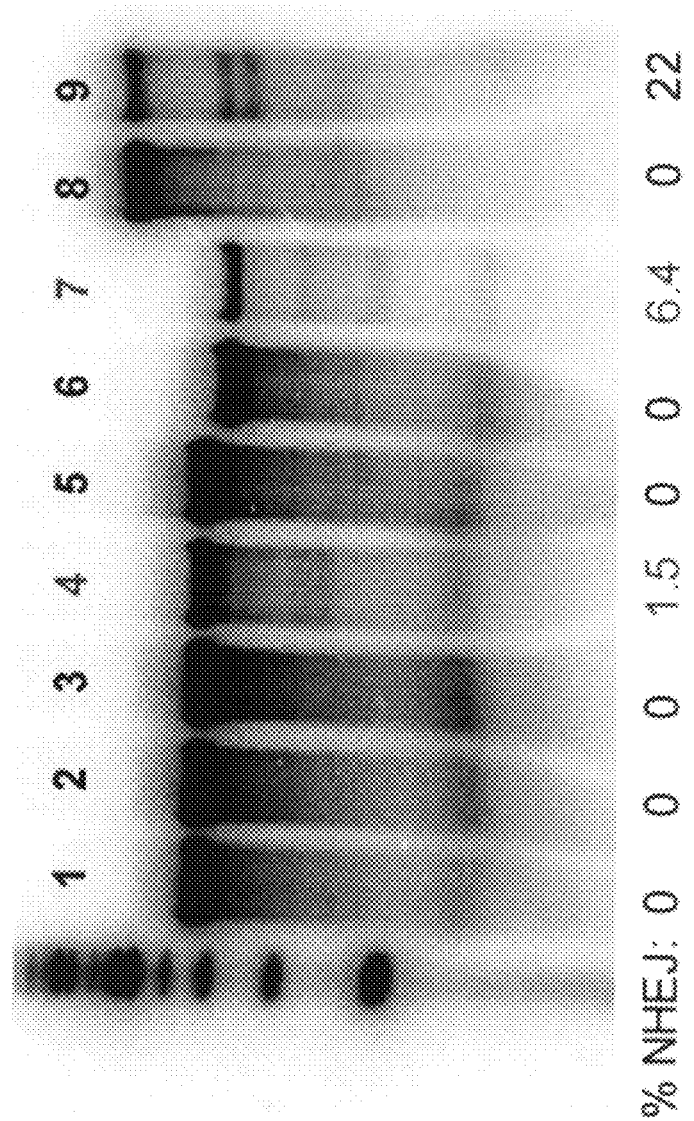
FIG. 5 is a blot showing activity of selected NME1-targeted ZFN pairs in human K562 cells. The percent of non-homologous end joining (NHEJ) is shown below each lane.

As shown in FIG. 5, the most active ZFN pair against NME1 in a human cultured cell line is 13674-13677. Furthermore, this ZFN pair was identified above as one of the most active proteins (FIG. 4A) that did not affect yeast cell growth (FIG. 4B).

One of the major problems associated with gene modification in human cell lines is the gradual loss of modified cells over time. With ZFNs, for example, after nine days in culture, the percent of gene modified cells often drops off, perhaps due in part to the toxicity associated with overexpression of non-specific ZFNs. See, in Miller et al. (2007) *Nat. Biotechnol.* 25(7):778-85. Accordingly, to further confirm that the ZFN pair identified from the yeast reporter and toxicity screens remained nontoxic over time, the percent modification of human chromosomes in K562 cells was measured 2 days and 9 days after introduction of the ZFN pair 13674-13677.

Figure 6:
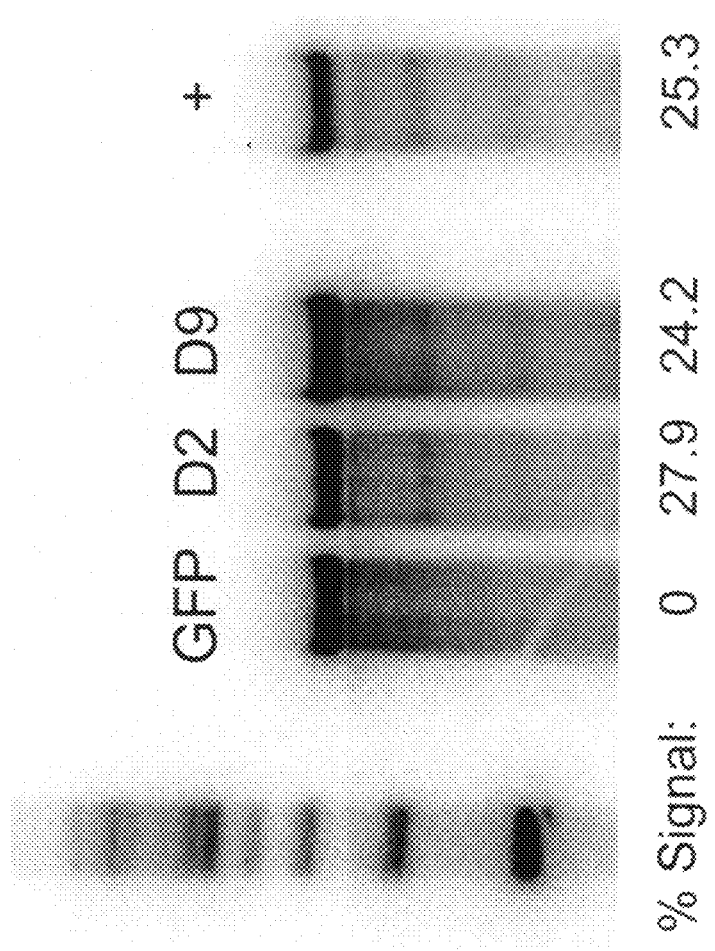
FIG. 6 is a blot depicting activity of NME-1 targeted ZFN pair 13674 and 13677 in human K562 cells. "GFP" refers to the green fluorescent protein negative control; "D2" refers to activity 2 days after introduction of the ZFN pair; "D9" refers to activity 9 days after introduction of the ZFN pair; and "+" refers to the positive control. The percent signal is indicated below each lane.

As shown in FIG. 6, the percent modification of the NME1 locus observed two days (D2) after transfection of the 13674-13677 ZFN pair was maintained after nine days (D9) of culture.

These results demonstrate the yeast system described herein accurately predicts in vivo ZFN activity and, in addition, also accurately predicts which ZFNs give a persistent signal over time.

Example 5

Identification of Persistently Biologically Active PD1-Specific ZFNs

ZFNs were assembled against the human PD1 gene and were tested by ELISA and CEL1 assays as described in Miller et al. (2007) *Nat. Biotechnol.* 25:778-785 and U.S. Patent Publication No. 20050064474 and International Patent Publication WO2005/014791.

From this initial in vitro screen, two lead ZFN pairs were identified and submitted for elaboration in order to try to improve their efficiency. These pairs target exons 1 and 5 of this gene, respectively. The elaborated (improved) proteins were retested in a time-course experiment, essentially as described in Example 4 above. The results are summarized in Table 2 below.

TABLE 2

PD1 NHEJ

| Target | ZFN pair | % NHEJ | | |
|---|---|---|---|---|
| | | Day 3 | Day 7 | Day 9 |
| exon 1 | 12942/12946 | 8 | 7 | 5 |
| exon 1 | 12942/12947 | 10 | 6 | 6 |
| exon 5 | 12934/12971 | 11 | 6 | 1.5 |
| exon 5 | 12934/12972 | 11 | 7.5 | 2 |

As shown in Table 2, treatment of cells with ZFNs against exon 5 causes the loss of a greater proportion of genome-edited cells from the population, while the genome-editing signal in cells treated with ZFNs designed against exon 1 is much more stable.

These ZFNs were also tested in the yeast system for activity and for toxicity. Briefly, the PD1 cDNA (NM_005018) was subcloned into the SSA reporter construct and the assays performed as described in Example 3.

Figure 7:
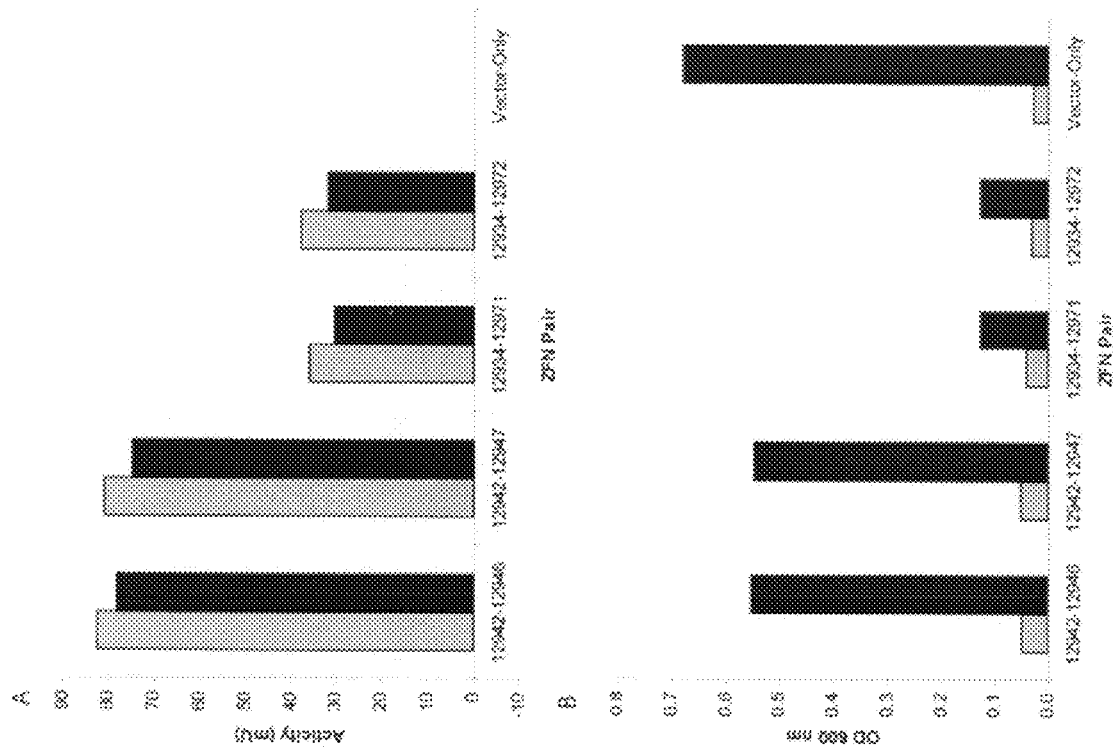
FIG. 7, panels A and B, are graphs showing results from SSA annealing assays and toxicity studies for PD1-ZFNs.

As shown in FIG. 7, the in vivo assay system clearly confirmed the activity of the PD1 ZFNs (FIG. 7A) and also determined the toxicity for all ZFNs targeting exon 5 (FIG. 7B). These results correlate with the loss of signal detected in human cells. Furthermore, the ZFNs designed against exon 1 show no impairment of yeast growth and maintain the signal in human cells.

Example 6

Identification of Biologically Active Zebrafish ZFNs

Panels of ZFNs were assembled against the zebrafish SLC24A5 ("golden") and notail ("NTL") genes and screened for activity in a yeast host cells comprising an SSA reporter construct with the appropriate target sequence. See, also, U.S. Patent Publication No. 20090203140.

Figure 9:
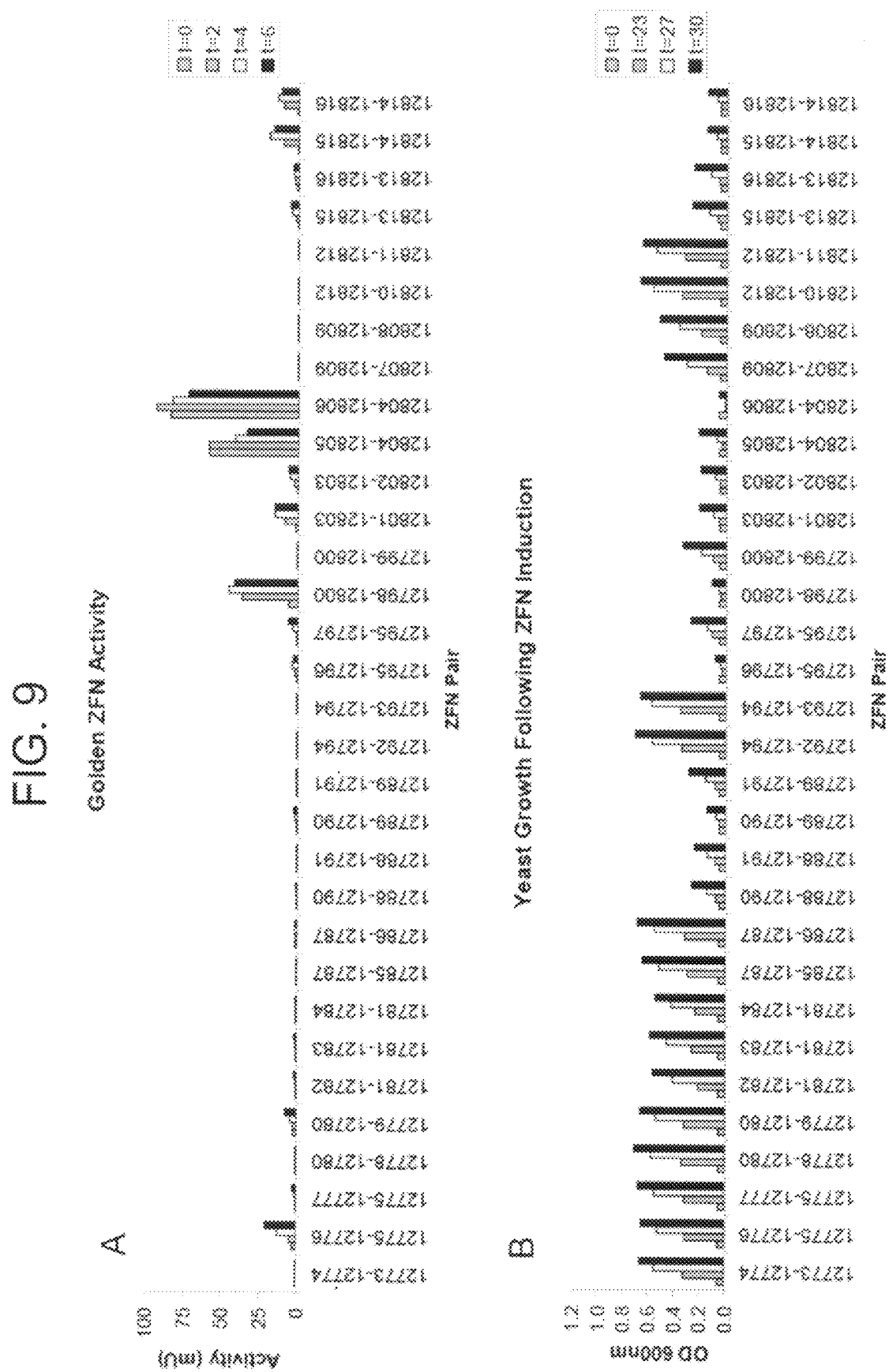
FIG. 9, panels A and B, are graphs showing results from SSA annealing assays and toxicity studies for ZFNs targeted to the golden gene of zebrafish.
Figure 10:
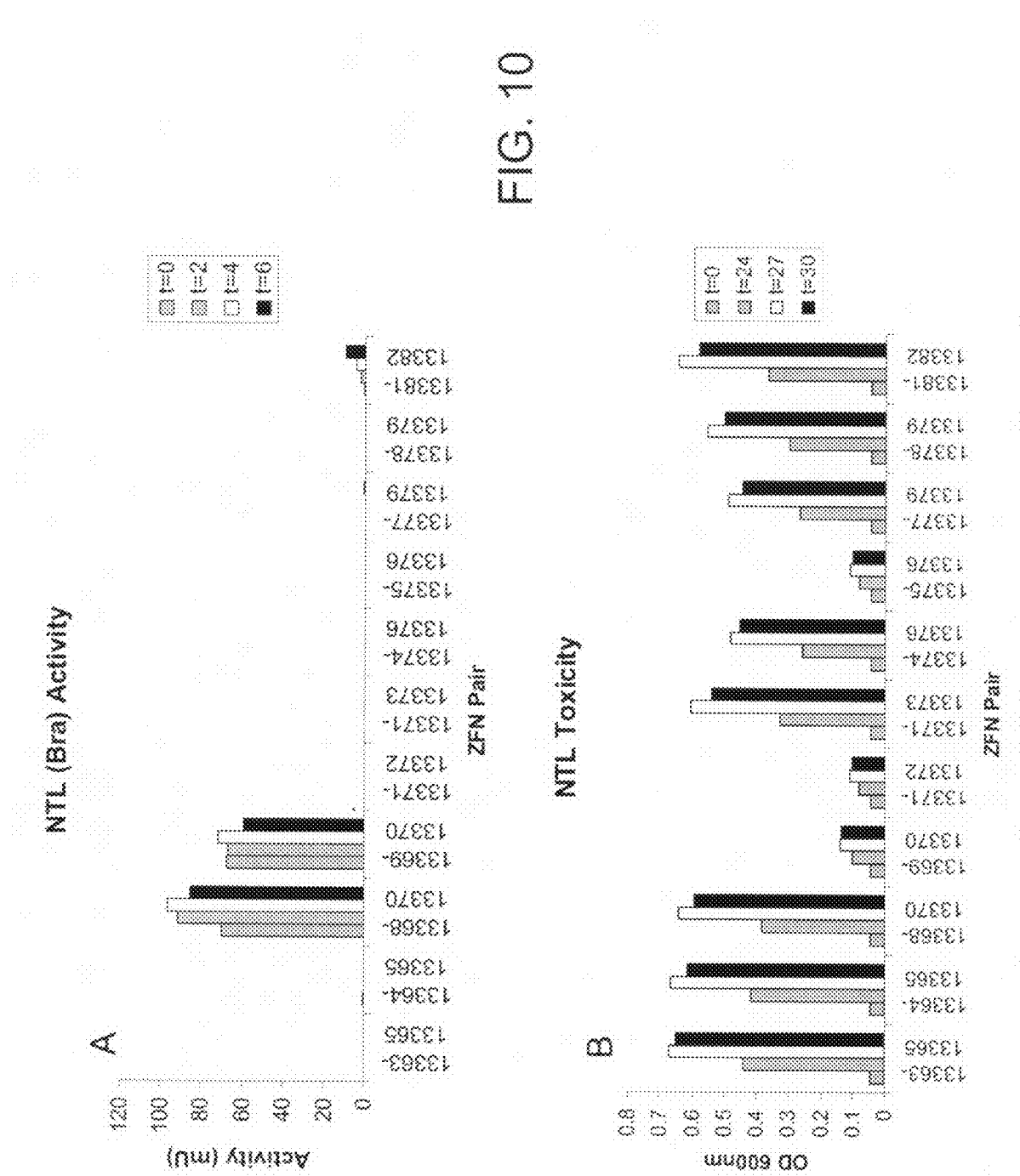
FIG. 10, panels A and B, are graphs showing results from SSA annealing assays and toxicity studies for ZFNs targeted to the notail gene of zebrafish.

Results of yeast activity and toxicity screens are shown in FIG. 9A (golden ZFN activity); FIG. 9B (golden ZFN toxicity); FIG. 10A (notail ZFN activity); and FIG. 10B (notail ZFN toxicity).

Figure 11:
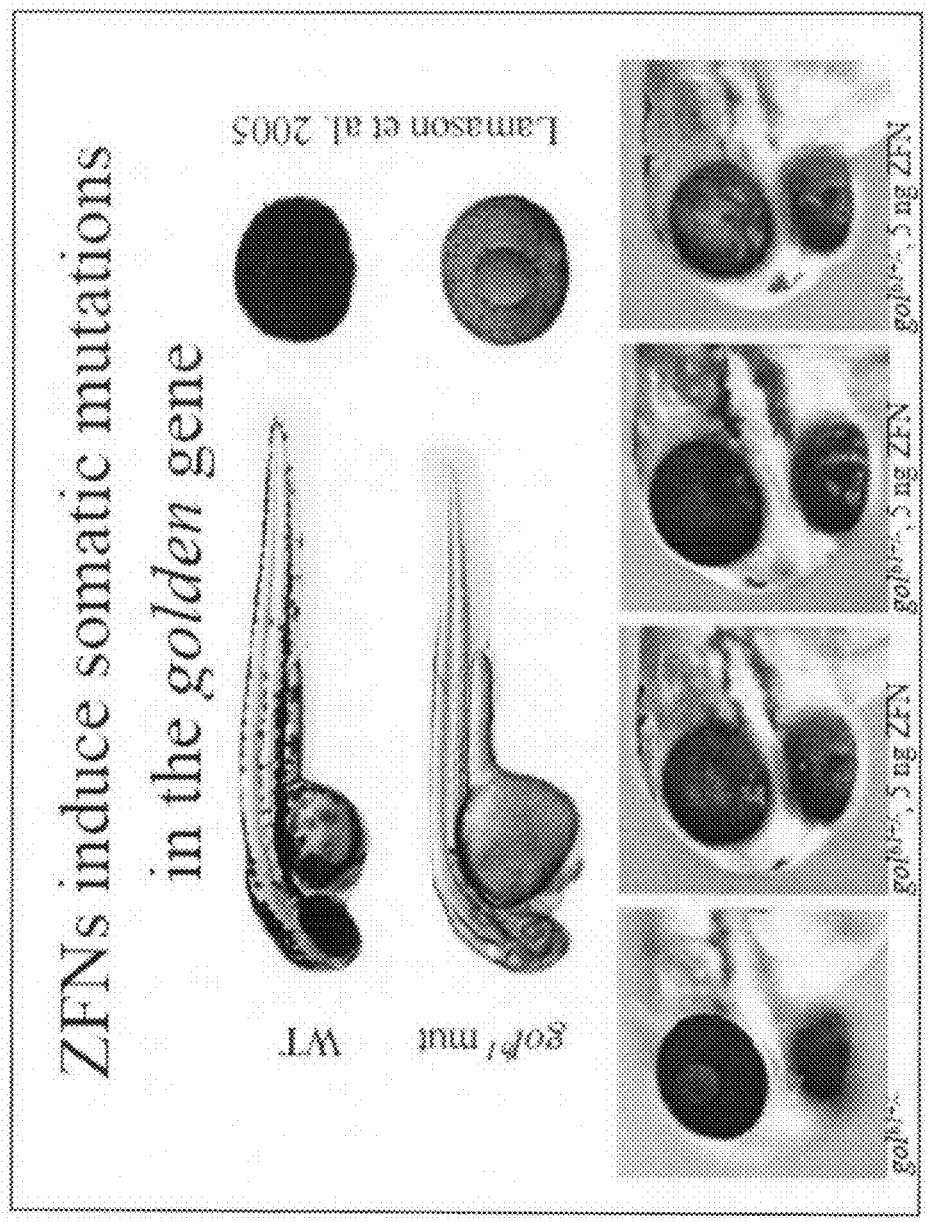
FIG. 11 shows pigmentation of zebrafish embryos upon disruption of the golden gene. The top panel shows a wild-type organism. The second panel from the top shows a zebrafish embryo when the golden gene was mutated as described in Lamason et al. (2005) Science 310(5755):1782-6. The left most bottom panel shows eye pigmentation in zebrafish with a gol$^{b1+/-}$ background. The 3 right bottom panels show eye pigmentation in gol$^{b1+/-}$ zebrafish injected with 5 ng of ZFN mRNA directed against golden gene.
Figure 12:
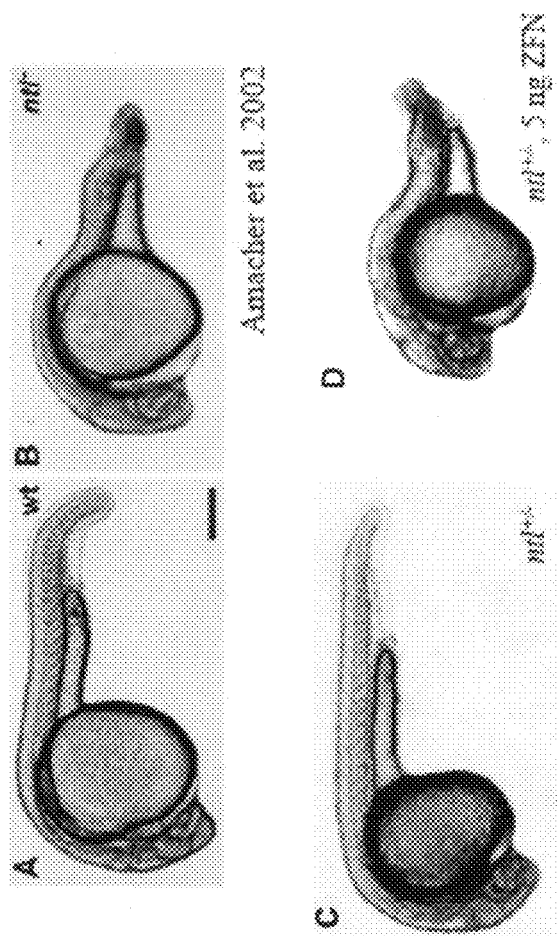
FIG. 12, panels A to D, show tail formation of zebrafish embryos upon disruption of the notail/Brachyury (ntl) gene.

ZFNs identified by the yeast screen were then injected into zebrafish embryos. Only embryos expressing the golden-ZFNs exhibited somatic mosaicism for pigmentation (FIG. 11). Similarly, only embryos expressing the NTL-ZFNs exhibited the forked-tail phenotype (FIG. 12).

Thus, the in vivo assay system described herein identified ZFNs that are biologically active in zebrafish.

Example 7

Identification of Active ZFN Variants Using a Selection-Based Screen

Active ZFN variants were selected using a positive and negative selection reporter yeast strain as follows. The reporter construct (FIG. 8) was generated and contained a homodimer recognition site for a well characterized ZFN (8266). See, Table 1 of U.S. Patent Publication No. 20080159996 for recognition helix and target sequence of 8266. The construct also contained a counterselectable gene (URA3) between the interrupted MEL1 gene as described in Example 4. In yeast cells containing this reporter, cells containing an inactive ZFN will be killed in the presence of 5-FOA permitting the selective expansion of cells containing active ZFN variants in the population. Similarly, cells containing an active ZFN cannot grow in the absence of uracil.

ZFNs containing five different linker sequences (different in length and/or amino acid residues) between the ZFP and the FokI cleavage domain were prepared and tested in the yeast screen assay described above. ZFNs with the wild-type linker sequence (8266) were active. In addition, two moderately active and two inactivate variants were identified. A pool of ZFNs containing 8266 as well as the two moderately active and two inactive variants was prepared and tested in a yeast counterselection assay as follows.

Figure 13:
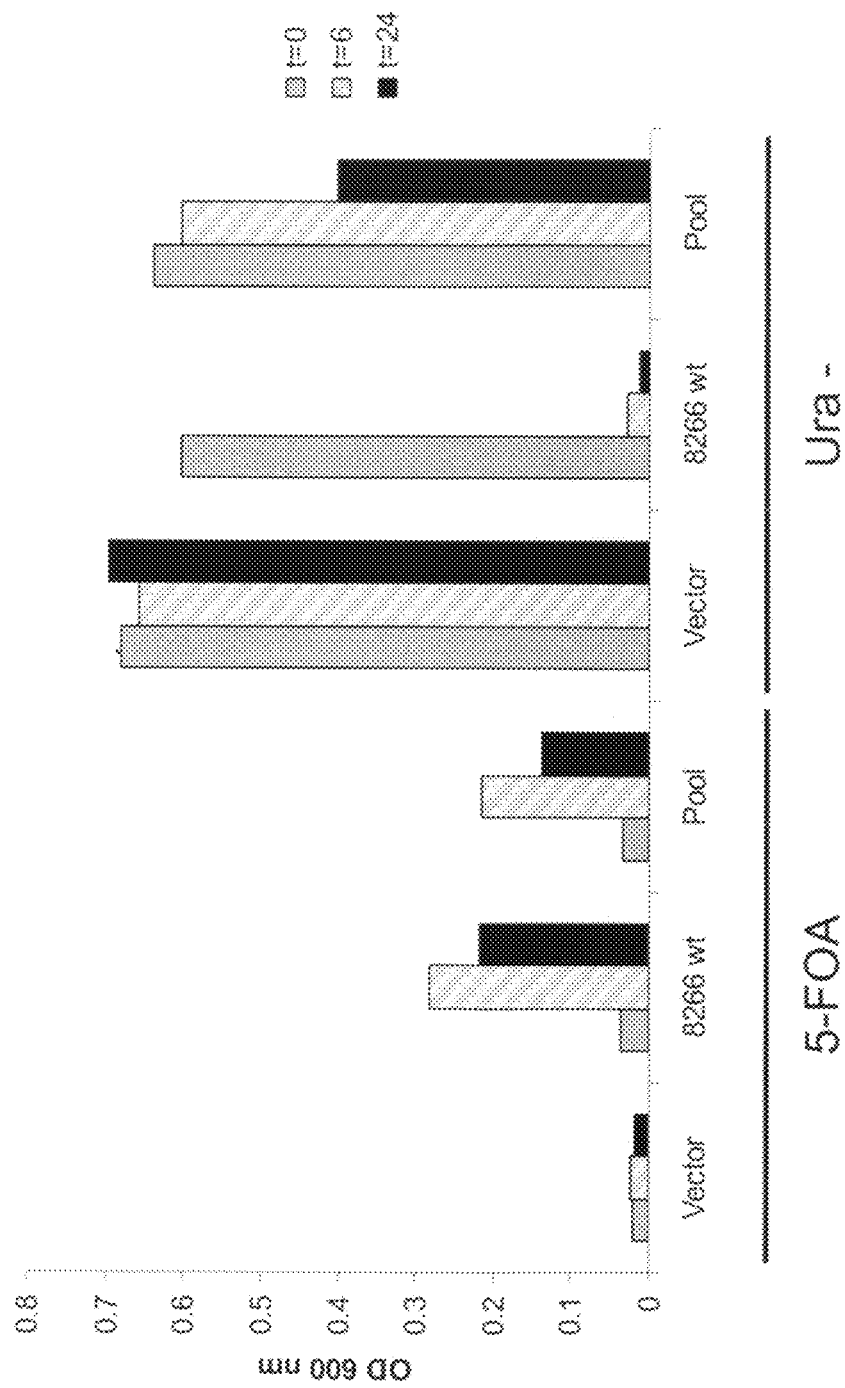
FIG. 13 is a graph showing results of growth assays of yeast reporter strains expressing various ZFN constructs following selection in counterselection medium (5-FOA) and negative selection in ura-media. Yeast cells were transformed with either an empty expression vector ("vector"), a ZFN ("8266") or a pool of the same ZFN with five different linker sequences ("pool"). The left part of the graph shows the growth in the presence of 5-FOA. The right part of the graph shows growth of the yeast cells in absence of uracil. The bars over each label shows growth after the indicated periods of ZFN induction. The left bar (t=0) shows growth with no ZFN induction; the middle bar shows growth when ZFNs were induced for 6 hours (t=6) and the right bar shows when ZFNs were induced for 24 hours (t=24).

The ZFN variants were mixed in equimolar ratios and the reporter strains was transformed as described in Example 4. ZFN induction was performed as in Example 4 for 6 and 24 hours. After a recovery period of 16 hours, the cells were diluted 100 fold in media containing the counterselecting agent 5-FOA for 20 hours. As a verification that the active ZFNs had cleaved the URA3 gene, the cells were similarly diluted into media lacking added uracil. As can be seen from the right portion of FIG. 13, the cells containing active ZFN (SBS 8266) were not able to grow in the absence of uracil. As shown in FIG. 13, yeast growth is observed only when active ZFN were used to transform the reporter strain.

The cells were then harvested, total DNA was extracted from the yeast population and individual plasmids were obtained by retransforming into *E. coli*. Twelve colonies were picked at random and sequenced. Of the 12, 9 sequences matched the wild-type linker, 3 sequences corresponded to the moderately active variants, while no sequences corresponded to the inactive variants. Thus, it was possible to specifically enrich the most active variants within a population of ZFN variants.

These data validate the yeast system for the identification of biologically active ZFN pairs from a set of biochemically active variants and also demonstrate the use of the toxicity assay for the determination of their relative specificity.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A yeast host cell comprising a genome and an integrated exogenous sequence, the integrated exogenous sequence comprising a reporter construct for detecting double-stranded cleavage by a pair of zinc finger nucleases, the reporter construct comprising
   (i) overlapping and non-functional sequences of a reporter gene separated by an exogenous sequence comprising a counterselectable gene, a sequence encoding antibiotic resistance and a non-coding sequence comprising target sequences recognized by at least two different pairs of zinc finger nucleases, wherein the target sequences comprise endogenous mammalian or plant sequences not present in the yeast cell; and
   (ii) regions of homology to the genome of the yeast host cell flanking the overlapping and non-functional reporter gene sequence,
   wherein the reporter gene is capable of being reconstituted when the target sequences are cleaved by the pair of zinc finger nucleases.

2. The host cell of claim 1, wherein the reporter gene is operably linked to a promoter sequence.

3. The host cell of claim 2, wherein the promoter is constitutive.

4. The host cell of claim 2, wherein the promoter is an inducible promoter.

5. The host cell of claim 1, wherein the reporter gene encodes an enzyme.

6. The host cell of claim 5, further comprising a sequence encoding a selectable marker.

7. A method of identifying a pair of zinc finger nucleases that induce cleavage at a specific target site, the method comprising the steps of:
   introducing one or more expression constructs that expresses the pair of zinc finger nucleases into host cells according to claim 1, wherein the reporter construct comprises a target sequence recognized by the pair of zinc finger nucleases;
   incubating the cells under conditions such that the pair of zinc finger nucleases is expressed;
   selecting the incubated cells in medium containing a counterselecting agent; and
   measuring cell growth of the selected cells, wherein increased levels of cell growth are correlated with increased zinc finger nuclease-induced cleavage of the target sequence.

8. A method of ranking a panel of zinc finger nuclease pairs for their activity in inducing cleavage at a specific target site, the method comprising the steps of:
   introducing one or more expression constructs encoding the zinc finger nuclease pairs of the panel into separate host cells according to claim 1, wherein the reporter construct in the host cell comprises a target sequence recognized by the zinc finger nuclease pair;
   incubating the cells under conditions such that the zinc finger nuclease pairs are expressed;
   selecting the incubated cells in medium containing a counterselecting agent;
   measuring cell growth of the selected cells, wherein increased levels of cell growth are correlated with increased zinc finger nuclease-induced cleavage of the target sequence; and
   ranking the nucleases according to levels of cell growth.

9. A method of predicting in vivo cleavage activity of a pair of zinc finger nucleases, the method comprising the steps of:
   introducing an expression construct encoding the pair of zinc finger into a host cell according to claim 1, wherein the reporter construct comprises a target sequence recognized by the pair of zinc finger nucleases;
   incubating the cells under conditions such that the pair of zinc finger nucleases is expressed;
   selecting the incubated cells in medium containing a counterselecting agent; and
   measuring cell growth of the selected cells, wherein increased levels of cell growth are correlated with increased zinc finger nuclease-induced cleavage of the target sequence;
   wherein cell growth is predictive of a pair of zinc finger nucleases that will be active in vivo.

10. The method of any one of claim 7, 8 or 9, wherein the cell growth is determined by spectrophotometry.

* * * * *